US008507650B2

(12) United States Patent
Gabriel et al.

(10) Patent No.: US 8,507,650 B2
(45) Date of Patent: Aug. 13, 2013

(54) USE OF BACTERIOPHAGE OUTER MEMBRANE BREACHING PROTEINS EXPRESSED IN PLANTS FOR THE CONTROL OF GRAM-NEGATIVE BACTERIA

(75) Inventors: Dean W. Gabriel, Alachua, FL (US); Joseph D. Reddy, Alachua, FL (US)

(73) Assignees: Integrated Plant Genetics, Inc., Alachua, FL (US); University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 13/487,595

(22) Filed: Jun. 4, 2012

(65) Prior Publication Data

US 2012/0316104 A1 Dec. 13, 2012

Related U.S. Application Data

(60) Division of application No. 12/176,874, filed on Jul. 21, 2008, now Pat. No. 8,212,110, which is a continuation-in-part of application No. 10/556,563, filed as application No. PCT/US2004/015099 on May 14, 2004, now Pat. No. 7,919,601.

(60) Provisional application No. 60/470,799, filed on May 14, 2003, provisional application No. 60/950,749, filed on Jul. 19, 2007.

(51) Int. Cl.

| | |
|---|---|
| ***C07K 17/00*** | (2006.01) |
| ***C07K 1/00*** | (2006.01) |
| ***C12N 5/00*** | (2006.01) |
| ***C12N 5/04*** | (2006.01) |

(52) U.S. Cl.
USPC ........... 530/350; 530/324; 530/325; 530/326; 530/327; 514/2.8; 435/410; 435/418

(58) Field of Classification Search
None
See application file for complete search history.

(56) References Cited

U.S. PATENT DOCUMENTS

| | | | |
|---|---|---|---|
| 6,783,930 | B1 | 8/2004 | Pelletier et al. |
| 6,858,707 | B1 | 2/2005 | Wei et al. |
| 7,919,601 | B2 | 4/2011 | Ramadugu et al. |
| 8,212,110 | B2 | 7/2012 | Gabriel et al. |
| 2009/0136914 | A1 | 5/2009 | Ramadugu et al. |

FOREIGN PATENT DOCUMENTS

WO WO 2004/104169 A2 12/2004

OTHER PUBLICATIONS

Fourgoux-Nicol et al (1999), Plant Molecular Biology 40: 857-872.*
Pompejus et al. Accession No. AAB79429; deposited 2001.*
Masaya Oki, et al., "Functional and structural features of the holing HOL protein of the *Lactobacillus plantarum* phage Φgle: analysis in *Escherichia coli* system", Gene 197 (1997) pp. 137-145.
Fourgoux-Nicol et al. "Isolation of rapeseed genes expressed early and specifically during development of the male gametophyte", (1999) Plant Molecular Biology 40:857-872.
Guo et al. "Protein tolerance to random amino acid change", PNAS (2004), 101:9205-9210.
Keshin et al. "A new, structurally nonredundant, diverse data set of protein-protein interaces and its implications", Protein Science (2004), 13:1043-1056.
English translation of Office Action in Chinese Patent Application No. 200880107780.2, mailed on Nov. 30, 2012.

* cited by examiner

*Primary Examiner* — Medina A Ibrahim
(74) *Attorney, Agent, or Firm* — Cooley LLP

(57) ABSTRACT

The present invention provides compositions and methods for killing or suppressing growth of Gram-negative bacteria that infect, infest or cause disease in plants, including pathogenic, saprophytic and opportunistic microbes that cause disease in plants and food borne illness in people or in animal feed.

9 Claims, 6 Drawing Sheets

USE OF BACTERIOPHAGE OUTER MEMBRANE BREACHING PROTEINS EXPRESSED IN PLANTS FOR THE CONTROL OF GRAM-NEGATIVE BACTERIA

CROSS-REFERENCE TO RELATED APPLICATIONS

This application claims benefit as a Divisional of U.S. application Ser. No. 12/176,874, filed Jul. 21, 2008, now U.S. Pat. No. 8,212,110, which claims benefits as a Continuation-In-Part of U.S. application Ser. No. 10/556,563, filed Nov. 14, 2005, now U.S. Pat. No. 7,919,601, which claims benefit as a U.S. National Stage Application under 35 U.S.C. 371 of PCT/US2004/015099, filed May 14, 2004, which claims the benefit of U.S. Provisional Application Ser. No. 60/470,799, filed May 14, 2003, each of which are herein incorporated by reference in their entireties for all purposes. The present application also claims the benefit of U.S. Provisional Application No. 60/950,749, filed Jul. 19, 2007, which is herein incorporated by reference in its entirety for all purposes.

DESCRIPTION OF THE TEXT FILE SUBMITTED ELECTRONICALLY

The contents of the text file submitted electronically herewith are incorporated herein by reference in their entirety: A computer readable format copy of the Sequence Listing of the Sequence Listing (filename: INTE_004_02US_SeqList_ST25.txt, date recorded: May 30, 2011, file size 6 kilobytes).

FIELD OF THE INVENTION

The present invention relates to methods for killing or suppressing growth of Gram-negative bacteria that infect, infest or cause disease in plants, including pathogenic, saprophytic and opportunistic microbes that cause disease in plants and food borne illness in people or in animal feed.

BACKGROUND OF THE INVENTION

All publications and patent applications herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Plants grown for commercial agricultural purposes are nearly always planted as uniform monocultures; that is, single varieties of a given crop are mass-produced by vegetative propagation or by seed and are planted on a very large scale. When a pathogen or pest arrives that can overcome the natural disease or pest resistance of a given variety, severe economic losses can occur because of the practice of monoculture, sometimes involving loss of the entire crop in a given area. Control of diseases and pests using massive applications of agricultural chemicals is expensive, environmentally unsound and often impossible. For example, citrus canker disease, caused by a quarantined Gram-negative bacterial pathogen, *Xanthomonas citri*, has spread uncontrollably throughout Florida. As a second example, the Gram-negative bacterial pathogen Ca. *Liberibacter asiaticus* is a USDA Select Agent (potential bioterrorist agent) that was introduced into Florida in 2005 and has spread uncontrollably throughout Florida. This pathogen threatens world citrus production. As a third example, the Gram negative bacterial pathogen *Ralstoma solanacearum* Race 3 Biovar 2 has been introduced into the U.S. numerous times and is such a serious threat to U.S. potato production that it is also a listed USDA Select Agent. This pathogen has been introduced into the U.S. by infecting geranium plants, but asymptomatically, so that detection of the pathogen is delayed.

As a fourth and final example, serious human illness and even deaths have been reported due to the Gram-negative bacterium *Escherichia coli*, which is capable of internally infecting—not just contaminating—certain crop plants such as spinach, alfalfa sprouts and mung bean sprouts. Several outbreaks of *Salmonella* and *E. coli* O157:H7 associated with organically grown sprouts and mesclun lettuce have been reported (Doyle, M. P. 2000. Nutrition 16: 647-9). According to the FDA in its web report of the 2006 outbreak of *E. coli* in contaminated spinach "To date, 204 cases of illness due to *E. coil* O157:H7 infection have been reported to the CDC including 31 cases involving a type of kidney failure called Hemolytic Uremic Syndrome (HUS), 104 hospitalizations, and three deaths. The first death was an elderly woman in Wisconsin; the second death, a two-year-old in Idaho; and the third death, an elderly woman in Nebraska." Conventional plant breeding to control such diseases of plants or food-borne contamination has proven to be impossible. There is therefore an urgent and pressing need for gene engineering techniques to provide plants, including carrier plants such as geraniums, with disease and pest resistance against diseases and pests that they naturally are susceptible to, or tolerant of.

A wide variety of antibacterial and antifungal proteins have been identified and their genes isolated from both animals and plants. Because of the major differences in the structures of fungal, Gram-positive bacterial and Gram-negative bacterial cell walls, many of these proteins attack only fungi or Gram positive bacteria, which have cell walls that are exposed directly to the environment. Gram negative bacteria do not have cell walls that are exposed directly to the environment. Instead, their cell walls are enveloped and protected by a unique outer membrane structure, the lipopolysaccharide (LPS) barrier, which provides a very effective additional barrier to protect their cell walls against most eukaryotic defenses, particularly plant defenses. The great majority of the pathogens listed by the USDA as Select Agents are bacterial pathogens, and all of these are Gram negative.

The LPS provides an effective defense to Gram negative bacteria against externally produced enzymes that can effectively degrade the bacterial cell wall (also called the murein layer), including the relatively thick but exposed cell walls of Gram-positive bacteria and fungi. For example, lysozymes are antimicrobial agents found in mammalian cells, insects, plants, bacteria and viruses that break bacterial and fungal cell walls, specifically cleaving bonds between the amino sugars of the recurring muropeptides (C-1 of N-acetylmuramic acid and C-4 of N-acetylglucosamine of microbial cell walls (Ibrahim et al. 2001 and references therein). Some lysozymes also are pleiotropically lytic proteins, meaning they are active in killing Gram-negative and Gram-positive bacteria, but this activity is not due to the enzymatic action of lysozyme, but specifically due to a short, linear peptide fragment that is a degradation product of some lysozymes; it is the linear degradation product of the lysozyme that penetrates the LPS barrier and the cell wall (but without harming either), reaching the inner membrane and permeabilizing the inner membrane, resulting in lysis (During et al, 1999; Ibrahim et al. 2001). However, this linear peptide activity does not work well in plants (see below).

Those antimicrobial proteins demonstrated to kill Gram-negative bacteria are mostly small peptides (proteins of less than 50 amino acids in length) that are amphipathic and positively charged, so that they are attracted to the negatively charged Gram negative outer membrane, are small enough to penetrate can penetrate the exposed LPS, and also the relatively thin Gram negative cell wall. These peptides usually act to permeabilize the inner membrane, directly causing cell death. During the last two decades, over 500 antimicrobial peptides have been discovered in viruses, insects, plants and animals (Jaynes et al, 1987; Mitra and Zhang, 1994; Broekaert et al. 1997; Nakajima et al, 1997; Vunnam et al, 1997). The best described of these are peptides having broad spectrum activity in the source organism and in artificial media against viruses, bacteria, fungi, parasites and even tumor cells (Hancock and Lehrer, 1998).

The largest described group by far of these antimicrobial peptides are linear (eg., cecropins, attacins and magainins). However, linear peptides are not found naturally in plants and most linear peptides are rapidly degraded by plant proteases. For example, cecropin B is rapidly degraded when incubated with intercellular plant fluid, with a half-life ranging from about three minutes in potato to about 25 hours in rice (Owens & Heutte, 1997). Transgenic tobacco plants expressing cecropins have only slightly increased resistance to (Gram-negative) *Pseudomanas syringae* pv. *tabaci*, the cause of tobacco wildfire (Huang et al 1997). Synthetic cecropin analogs Shiva-1 and SB-37, expressed from transgenes in potato plants, only slightly reduced bacterial infection caused by (Gram-negative) *Erwinia carotovora* (Arce et al 1999). Transgenic apple expressing the SB-37 peptide showed only slightly increased resistance to (Gram-negative) *E. amylovora* in field tests (Norelli et al 1998). Similarly, transgenic potatoes expressing attacin showed resistance to bacterial infection by *E. carotovora* (Arce et al 1999) and transgenic pear and apple expressing attacin genes have also shown slightly enhanced resistance to *E. amylovora* (Norelli et al 1994; Reynoird et al 1999). Attacin E was also found to be rapidly degraded by plants (Ko et al 2000). Transgenic tobacco plants expressing a synthetic magainin analog that had been modified to be less sensitive to extracellular plant proteases were only slightly resistant to the bacterial pathogen *E. carotovora* (Li et al 2001).

The disulfide-linked peptides (e.g. defensins, prophenins and thaumatins) show more promise of stability when expressed in plants, but resistance has either been weak, not demonstrated, or cytotoxicity issues have emerged. Hen egg-white lysozyme genes (with lytic ability) have been used to confer weak Gram-negative bacterial disease resistance to transgenic tobacco plants (Trudel et al 1995; Kato et al 1998). Bacteriophage T4 lysozyme has also been reported to slightly enhance resistance in transgenic potato against *E. carotovora* (During et al 1993; Ahrenholz et al., 2000) and in transgenic apple plants against *E. amylovora* (Ko 1999). However, as mentioned previously, the action of lysozyme against Gram-negative bacteria is specifically due to a short lytic peptide fragment (Ibrahim et al. 2001) that is presumably sensitive to protease. Thaumatins exhibit the widest range of antimicrobial activity so far characterized, but also exhibit potent cytotoxic effects on eukaryotic cells (Taguchi et al 2000). Defensins, produced by plants, mammals and insects, are characterized by complex β-sheet structures with several disulfide bonds that bind and disrupt microbial plasma membranes. A plant defensin from alfalfa gave robust resistance to a fungal pathogen (Guo et al 2000) and defensins from spinach were active in vitro against Gram positive and Gram negative bacteria (Segura et al. 1998). However, human illnesses have resulted from both alfalfa and spinach infected with enteric bacteria; evidently these defensins are either not triggered by these bacteria or they are ineffective against these bacteria. More effective antibacterial agents are urgently needed to protect crop plants.

Nonenzymatic, antimicrobial peptides are abundant in nature but of limited value in transgenic plants, primarily due to degradation by plant proteases. In addition, some Gram-negative bacteria are resistant to antimicrobial peptides even in culture media, due to variations in the chemical structure of the LPS (Gutsmann et al., 2005). This may help explain why plant pathogenic bacteria can overcome host plant defensins. To date, no antimicrobial peptide has proved more than marginally effective against Gram-negative bacteria when expressed in plants. More efficacious methods to control plant disease are urgently needed.

By contrast with bacterial pathogens of animals, the vast majority of bacterial pathogens of plants are all Gram negative. As mentioned above, the distinguishing feature of Gram-negative bacteria is the presence of the LPS, which forms an outer membrane that completely surrounds the cell wall. Mutations affecting the structure of the LPS of a (Gram-negative) bacterial plant pathogen of citrus caused the pathogen to die out very quickly on citrus, but not on bean (Kingsley et al., 1993), indicating the importance of the LPS structure in evading specific plant phytochemical defenses. In addition, mutations affecting multidrug efflux in Gram-negative bacteria cause the bacteria to die out rapidly in plants, highlighting the role of low molecular weight plant defense compounds (phytoalexins) in plant defense, and further indicating the importance of the intact LPS of Gram-negative in resisting plant defense compounds (Reddy et al., 2007). Multidrug efflux requires an intact LPS for function.

Animals have a unique set of innate defenses against microbial invasion that is independent of prior exposure to pathogens (Hoffman et al., 1999). Among these are the lytic peptides discussed above, and also the neutrophil, a white blood cell that is part of the innate immune system. Neutrophils produce a variety of protein and peptide antibiotics that kill microorganisms. Among these is the bactericidal/permeability increasing (BPI) protein, which is a potent antimicrobial protein that is primarily active towards Gram negative bacteria (Levy, 2000). BPI is not toxic to Gram positive bacteria, fungi or animal cells, but rather attacks the LPS layer of Gram negative cells, disrupting its structure, and eventually attacking the inner membrane and causing lysis (Mannion et al., 1990). A hallmark of BPI proteins is their strongly cationic, lysine rich nature and their opsonic or immune system activation ability (Levy et al., 2003). Members of the BPI protein family include lipopolysaccharide binding protein (LBP), lung specific X protein (LUNX), palate, lung and nasal epithelial clone (PLUNC) and parotid secretory protein (PSP), many of which have been identified by bioinformatics techniques with up to 43% identity between family members (Wheeler et al. 2003). There are numerous patents covering use of BPI and certain smaller peptide derivatives (for example, U.S. Pat. No. 5,830,860 and U.S. Pat. No. 5,948,408).

Antimicrobial Bacteriophage Proteins.

All bacteriophages must escape from bacterial host cells, either by extrusion from the host cell, as with filamentous phages, or by host cell lysis from within. Host cell lysis from within requires two events: ability to penetrate the inner membrane of both gram negative and gram positive bacteria, and ability to depolymerize the murein layer, which is relatively thick in gram positive cell walls.

Bacteriophage penetration of, and egress through, the inner membrane is accomplished in many, but evidently not all, phage by use of small membrane-localized proteins called "holins" that appear to accumulate in the bacterial inner membrane until reaching a specific concentration, at which time they are thought to self-assemble to permeabilize the inner membrane (Grundling et al., 2001; Wang et al. 2000; Young et al., 2000). The terms "holin" and "holin-like" are not biochemically or even functionally accurate terms, but instead as used herein refer to any phage protein with at least one transmembrane domain that is capable of permeabilizing the inner membrane, thereby allowing molecules other than holins that are normally sequestered in the cyctoplasm by the inner membrane, including proteins such as endolysins, to breach or penetrate the inner membrane to reach the cell wall. The biochemical function(s) of holins is speculative; most, if not all of the curent knowledge on holins is based on the λ phage S protein (Haro et al. 2003).

Holins are encoded by genes in at least 35 different families, having at least one transmembrane domain and classified into three topological classes (classes I, II, and III, with three, two and one transmembrane domains [TMD], respectively), all with no detected orthologous relationships (Grundling et al., 2001). At least two holins are known to be hemolytic and this hemolytic function has been hypothesized to play a role in the pathogenesis of certain bacteria towards insects and nematodes (Brillard et al., 2003). Only a few have been partially characterized in terms of in vivo function, leading to at least two very different theories of how they may function. The most widely accepted theory is that holins function to form oligomeric membrane pores (Graschopf & Blasi, 1999; Young et al., 2000).

Depolymerization of the murein layer is accomplished by lytic enzymes called endolysins. There are at least three functionally distinct classes of endolysins: 1) glucosaminidases (lysozymes) that attack the glycosidic linkages between the amino sugars of the peptidoglycan; 2) amidases that attack the N-acetylmuramoyl-L-alanine amide linkage between the glycan strand and the cross-linking peptide, and 3) endopeptidases that attack the interpeptide bridge linkages (Sheehan et al., 1997). Endolysins are synthesized without an export signal sequence that would permit them access to the peptidoglycan (murein) layer, and they therefore usually accumulate in the cytoplasm of phage infected bacteria until they are released by the activity of holins (Young and Blasi, 1995).

Lysozymes have been suggested as useful antibiotics that can be used as external agents against both Gram-positive and Gram-negative bacteria because at least some of them are multifunctional (During et al., 1999). This dual functionality is based on the finding that both phage T4 and hen egg white lysozyme have both glucosaminidase activity as well as amphipathic helical stretches that allow them to penetrate and disrupt bacterial, fungal and plant membranes (During et al., 1999). The microbicidal activity of lysozymes can be affected by C-terminal additions; additions of hydrophobic amino acids decreased activity against Gram positive bacteria, but increased activity against Gram negative *E. coli* (Arima et al., 1997; Ito et al., 1997). Additions of histidine, a hydrophilic amino acid, to T4 lysozyme doubled its antimicrobial activity against Gram-positive and Gram-negative bacteria (During et al., 1999).

The nonenzymatic, microbicidal function of lysozymes appeared to be due to amphipathic C-terminal domains that could be mimicked by small synthetic peptides modeled after the C-terminal lysozyme domains (During et al., 1999). As described above, transgenic plants have been created that express lysozymes and give some resistance to certain plant pathogens. Since most endolysins accumulate to high titers within the bacterial cell without causing lysis, endolysins other than certain lysozymes such as T4 would not be expected to attack Gram-negative bacteria if externally applied, since Gram-negative bacteria are surrounded with an outer membrane comprised of LPS and a lipid bilayer that would protect its murein layer from enzymatic attack just as effectively as its inner membrane does.

Attempts have been made to treat bacterial diseases of both animals and plants by use of intact bacteriophage. All of these attempts have severe limitations in their utility. For examples, U.S. Pat. No. 5,688,501 discloses a method for treating an infectious disease of animals using intact bacteriophage specific for the bacterial causal agent of that disease. U.S. Pat. No. 4,957,686 discloses a method for preventing dental caries by using intact bacteriophage specific for the bacterial causal agent of dental caries. Flaherty et al. (2000) describe a method for treating an infectious disease of plants using intact bacteriophage specific for the bacterial causal agent of that disease. In all these cases and in similar cases using intact bacteriophage, the bacteriophage must attach to the bacterial host, and that attachment is highly host specific, limiting the utility of the phage to specific bacterial host species, and sometimes specific bacterial host strains. In addition, for attachment to occur, the bacteria must be in the right growth phase, and the phage must be able to gain access to the bacteria, which are often buried deep within tissues of either animals or plants, or shielded by bacterial biofilms, formed in part by the secretion of bacterial extracellular polysaccharides (EPS).

Attempts have been made to treat *Erwinia amylovora* bacterial infections of pear and apple trees through the use of transgenic plants expressing an extracellular polysaccharide (EPS) degrading enzyme, EPS-depolymerase, derived from an *E. amylovora* phage. However, the level of resistance achieved was weak, at best, and the phage EPS-depolymerase was very specific for the EPS from *E. amylovora*. More efficacious, and more generally applicable, strategies are clearly needed.

Attempts have been made to treat gram-positive bacterial diseases of animals, but not plants, by use of lytic enzyme preparations extracted from bacteriophage infected bacteria or from bacteria expressing bacteriophage genes. These, too, have serious limitations. For example, U.S. Pat. No. 5,985,271 discloses a method of treating an animal disease caused by a specific gram positive bacterium, *Streptococcus*, by use of a crude specific endolysin preparation. Similarly, U.S. Pat. No. 6,017,528 discloses a method of preventing and treating *Streptococcus* infection of animals by use of a crude specific endolysin preparation. Similarly, WO 01/90331 and US 2002/0058027 disclose methods of preventing and treating *Streptococcus* infection of animals by use of a purified preparation consisting of a specific endolysin. In all of these cases, the enzyme preparations must be purified, buffered, prepared for delivery to the target areas and preserved at the target site. In addition, the enzyme must be able to gain access to the infecting bacteria, and be present in sufficient quantity to kill the growing bacteria. None of these methods would be useful in the treatment of gram negative bacteria, because the endolysins could not penetrate the outer membrane of such bacteria.

Attempts have been made to treat both gram-positive and gram-negative bacterial diseases of animals, but not plants, by use of lytic enzyme preparations extracted from bacteriophage infected bacteria or from bacteria expressing bacteriophage genes. WO 01/51073, WO 01/82945, WO 01/019385, US 2002/0187136 and US 2002/0127215 disclose methods of preventing and treating a variety of gram positive and gram negative bacterial infections of animals by use of lytic enzymes that may optionally include specific "holin lytic enzymes" or "holin enzymes".

Since holins are not known to exhibit enzymatic function, and since examples of such holin lytic enzymes are not demonstrated or taught in WO 01/51073, WO 01/82945, WO 01/19385, US 2002/0187136 and US 2002/0127215, such enzymes appear to represent a theoretical and undemonstrated enzyme defined by reference to a desirable characteristic or property. As correctly stated elsewhere by the same inventors: "Holin has no enzymatic activity" (refer WO 01/90331, page 9 line 12). Lytic enzymes, which form the basis for the methods disclosed in all of these PCT publications, are internally defined: "The present invention is based upon the discovery that phage lytic enzymes specific for bacteria infected with a specific phage can effectively and efficiently break down the cell wall of the bacterium in question. At the same time, the substrate for the enzyme is not present in mammalian tissues." (WO 01/51073 paragraph 3, page 4). "The lytic enzymes produced by bacterial phages are specific and effective for killing select bacteria." (paragraph 2, page 7).

The term "holin enzyme" as used in Claim #3 of WO 01/51073 refers to the enzymes defined in Claim #1 as "the group consisting of lytic enzymes, modified lytic enzymes and combinations thereof." Similar references in the claims of WO 01/82945, WO 01/019385 and US 2002/0187136 and US 2002/0127215 may be found. None of these patent applications disclose or claim the use of holin or other phage derived proteins that lack enzymatic activity in any manner, including the formulation of a compound or method of treatment of animal or plant diseases.

WO 02/102405 discloses a method of preventing food poisoning in animals by inclusion of a purified preparation consisting of specific lytic enzymes and optionally, specific lytic "holin enzymes". Again, since holins are not known to exhibit enzymatic function, it is unclear as to what is taught or specified in the claims, other than a theoretical and undemonstrated enzyme defined by reference to a desirable characteristic or property.

It has been suggested that a specific endolysin from a bacteriophage that attacks a gram negative bacterial plant pathogen might be effective in providing resistance to that pathogen if the endolysin gene were cloned and expressed in plants (Ozawa et al., 2001). This suggestion is most unlikely, since endolysins other than T4 lysozyme are not known to penetrate bacterial membranes, and Gram-negative bacteria have a distinctive outer membrane, the LPS barrier, that provides a strong environmental barrier that is impermeable to most molecules.

It has been demonstrated that a gene from a bacteriophage infecting *Ralstoma solanacearum* encodes a lytic peptide that is capable of lysing several *R. solanacearum* strains (Ozawa et al. 2001). These authors suggested that this lytic peptide of undisclosed sequence might be used to enhance resistance against *R. solanacearum* in transgenic tobacco plants. However, there is no teaching or suggestion that this lytic peptide has bacteriocidal or bacteriostatic ability against any bacteria other than certain strains of *R. solanacearum*. Indeed, this evidently species-specific lytic peptide was expressed in *E. coli* without report of damage to the producing *E. coli* strains (Ozawa et al. 2001. This is not unexpected, since phage are highly specific for their bacterial host strains, and are normally limited in host range to a small subset of strains within a given host species. Methods are urgently needed to enhance resistance of plants against a broader range of pathogenic bacteria than a few strains of one pathogenic species.

In all previously published cases wherein phage genes are reported or suggested for use in a transgenic approach, the phage genes either encoded enzymes or, in one case, a highly species specific lytic peptide. In all previously published cases wherein phage preparations are incorporated, used or described, enzymes or enzyme preparations are involved. These enzymes must be purified, buffered, prepared for delivery to the target areas and preserved at the target site.

Thus, the prior art fails to teach or describe the identification or use of phage proteins with wide anti-microbial activity against Gram-negative bacteria. The prior art also fails to teach the use genes encoding phage proteins with wide anti-microbial activity against Gram-negative bacteria. In particular, the prior art fails to teach the use of phage proteins that are capable of destabilizing or permeabilizing the outer bacterial membrane (the bacterial lipopolysaccharide or LPS barrier) for the control of Gram negative bacterial infections of plants.

SUMMARY OF THE INVENTION

As described elsewhere herein, the present invention provides a method for outer membrane (LPS barrier) destabilization and permeabilization based upon the action of a previously undescribed bacteriophage protein called herein a Bacteriophage Outer Membrane Breaching (BOMB) protein. The present invention is based, in part, on our discovery that BOMBs not only breach but destabilize the Gram negative bacterial outer membrane. This action occurs not only if the BOMB is synthesized from within the bacterial cell, but in addition, occurs if the BOMB is applied externally as well. Activity of BOMBs in destabilization of the outer membrane presumably allows natural defense molecules secreted by plants and/or by other microbes to also breach the outer membrane of the target cells, thereby compromising the "barrier function" of the Gram negative outer membrane. Kingsley et al., (1993) provide strong evidence that the outer membrane of a plant pathogenic bacterium can function as a barrier in preventing plant defense molecules from the killing the bacteria. The invention also provides the incorporation of enzymatic cell wall depolymerization based upon peptidoglycan degrading bacteriophage proteins called endolysins and provides the incorporation of both BOMBs and endolysin function in a series of gene fusions and completely synthetic genes modeled on the gene fusions.

This invention provides: 1) methods for the identification of broad-spectrum BOMBs with a high level of nonenzymatic activity to breach microbial outer membranes and thereby increase the efficacy of both natural plant defense compounds and artificially applied compounds; 2) conditions required for maintaining and increasing the anti-microbial and anti-pest efficacy of BOMBs in gene fusions; 3) methods for effective targeting of BOMBs expressed in plants through use of a xylem enhanced promoter and a leader peptide to direct the BOMB protein to the plant apoplast and xylem; 4) methods for the control of Gram negative bacterial diseases of plants by expression of gene fusions involving BOMBs and BOMB fragments, C-terminal additions and leader peptides, and optionally, endolysins and/or lipases; 5) methods for increasing the shelf-life of cut flowers; and 6) transgenic plants useful for the production of novel antimicrobial proteins based upon BOMBs and BOMB fragments.

It has now been found by the present inventors that certain bacteriophage carry genes that encode proteins other than holins and endolysins that assist the phage in disrupting host cells, and specifically in disrupting the bacterial outer membrane or LPS layer found only in Gram negative bacteria. It has further been found that at least one such bacterial outer membrane breaching (BOMB) protein works from the outside of the cell to compromise the integrity of the bacterial LPS outer membrane. It has further been found that expression of a BOMB protein in Gram-negative bacteria inhibits the growth of the bacteria in culture, and that when coupled with detergents, lytic proteins such as certain lysozymes or plant defense compounds such as berberine chloride, growth inhibition and/or lysis occurs. Thus it has been discovered that a BOMB protein not only can have a direct inhibitory effect on Gram-negative bacteria in culture medium, but the effect is synergistic with enzymes that cause lysis or with compounds that are toxic. It has further been found that BOMB proteins compromise the integrity of the bacterial LPS barrier, but not the inner membrane. Further, the present inventors have: 1) identified, cloned and expressed *Xanthomonas pelargonii* phage Xp15 BOMB protein BC in *E. coil;* 2) operably fused the bombBC gene separately to plant promoters in a gene expression cassette; 3) expressed functional BombBC in multiple different transgenic plants, both monocot and dicot, including tomato, tobacco, geranium, citrus and rice; 4) killed or inhibited growth of many different Gram-negative pathogens of said plants, conferring enhanced disease resistance or immunity to said plants. Thus it has been discovered that BombBC, and more generally, BOMBs, may be functionally expressed in both monocot and dicot plants to enhance a plant's natural disease resistance mechanisms.

This invention therefore provides a general method for strongly enhancing disease resistance in plants against Gram-negative bacteria, whether plant pathogens or not, comprising introducing into the plant a gene expression cassette operably fusing: 1) a promoter that functions in plants; 2) a BOMB gene or gene fragment that functions to express active BOMB protein in plants; 3) a transcriptional terminator region that functions in plants; and 4) obtaining expression of said gene for BOMB production in said plants.

In one embodiment, the above expression cassette containing a BOMB gene or gene fragment that functions to express active BOMB protein in plants has a plant secretion signal sequence that functions in plants, operably fused to the amino terminus of the BOMB gene or gene fragment.

The present invention further provides nucleic acid molecules, operably linked to one or more expression control elements, including vectors comprising the isolated nucleic acid molecules. The nucleic acid sequences of the present invention can be naturally produced or synthetically produced using methods well know to those skilled in the art of nucleic acid preparation.

The invention further includes host cells transformed to contain the nucleic acid molecules of the invention and methods for producing a peptide, polypeptide or protein comprising the step of culturing a host cell transformed with a nucleic acid molecule of the invention under conditions in which the protein is expressed.

This invention provides vectors comprising the nucleic acid constructs of the present invention, as well as host cells, recombinant cells and transgenic tissues and organisms comprising the vectors of the present invention. More particularly, this invention provides such cells and transgenic tissues and organisms that are hemizygotic, heterozygotic or homozygotic for the nucleic acid constructs, wherein if the organism is a plant it can be monoploid, diploid or polyploid. It is an object of the present invention to provide such cells and transgenic tissues and organisms wherein they express a single copy or multiple copies of one or more BOMB proteins, or BOMB-like ortholog protein products of the present invention. Cells or transgenic tissues and organisms which express multiple copies of one of the BOMB proteins, or BOMB-like proteins, mutant BOMB or BOMB-like proteins, or BOMB or BOMB-like ortholog proteins, or which express more than one of the BOMB or BOMB-like proteins, mutant BOMB or BOMB-like proteins, or BOMB or BOMB-like ortholog proteins, or which express a translational or transcriptional gene fusion carrying an BOMB or BOMB-like protein may be desirable, for example, to produce broad-spectrum resistance or tolerance to a variety of different Gram negative bacteria, whether pathogens, opportunistic or saprophytic.

Gram-negative bacteria are in particular bacteria with an LPS, including but not limited to the following genera: *Agrobacterium, Burkholderia, Candidatus Liberibacter, Erwinia, Escherichia, Pseudomonas, Ralstonia, Salmonella, Shigella, Xanthomonas* and *Xylella.*

According to the invention it is possible to impart into virtually all plants resistance, or increased resistance, to Gram-negative bacteria, including, but not limited to, the above named pathogenic genera. There is a particular demand for the generation of such resistance in crop plants, both agronomic as well as horticultural, both for food crop use as well as ornamental. There is also a particular demand for the elimination of Gram-negative bacteria that are pathogenic to humans and animals that may be carried asymptomatically in some plants, such as fresh alfalfa and bean sprouts, lettuce and spinach. There is also a particular demand for the elimination of Gram-negative bacteria that may be carried asymptomatically in some plants, such as ornamental plants, including geraniums, but that can cause disease on other plants, such as crop plants, including potatoes. There is also particular demand for the elimination of USDA Select Agents that may be carried in crop plants such as citrus or geranium. There is also particular demand for the extension of shelf life of cut flowers, due to attack by Gram-negative bacteria that are saprophytic.

The present invention therefore also relates to a method for preparing transformed plant cells and plants, including seeds and all parts of plants, having increased resistance or immunity to Gram-negative bacterial infection or infestation, whether plant pathogenic or not. This method provides one or more BOMB genes, BOMB gene fusions, and the introduction of these genes and fusions into the genome of plant cells, followed by introduction of said genes into plant cells, regeneration of whole transformed plants from said cells, providing transgenic plants with resistance or immunity to disease, infection or infestation by Gram-negative bacteria. This invention describes the use of BOMB genes to control disease, infection and infestation in transgenic plants to: 1) control diseases otherwise affecting said transgenic plants, 2) to eliminate said transgenic plants from being carriers of diseases that affect other plants or animals (eg., nosocomial infestations or in animal feed), and 3) to prolong the shelf life of said transgenic plants if said plants are detached from roots (eg., cut flowers, grafting).

Multiple methods are used by those skilled in the art for introducing BOMB genes into plants or plant cells of dicots or monocots, including, but not limited to, use of *Agrobacterium tumefaciens* and various Ti-plasmid variations, use of *Rifizobium* spp, *Sinorhizobium* spp or *Mesorifizobium* spp. (Broothaerts et al., 2005) and various Ti-plasmid variations, use of electroporation, particle bombardment, fibrous silicon carbide whiskers or nonfibrous silicon carbide powder. Multiple methods are available to those skilled in the art for the regeneration of fully transgenic plants, including both dicots and monocots. The term "plants" as used herein denotes complete plants and also parts of plants, including seeds, tubers, cuttings, etc.

The invention further provides nucleic acid probes for the detection of expression of the BOMB or BOMB-like proteins of the present invention, or mutants, or homologs, or orthologs thereof, in for example, plants which either have been genetically altered to express at least one of said proteins or which may naturally express BOMB or BOMB-like proteins, or mutants, or homologs, or orthologs thereof.

This invention also provides the isolated nucleic acid sequence and its complement for Phage P15 ORF "BC" (bombBC: SEQ ID No. 1) and its corresponding amino acid sequence (SEQ ID No. 2) encoding the BombBC peptide. The invention further provides all possible variations and iterations of SEQ ID No. 1 including but not limited to its corresponding DNA sequences, coding sequences, genomic sequences, RNA sequences, interfering RNA (RNAi) sequences, double stranded RNAi (dsRNA) sequences, microRNA (miRNA) sequences, small interfering RNA (siRNA) sequences, expressed RNAi (eRNAi or eiRNA) sequences, antisense sequences, complementary DNA (cDNA) sequences, inverse cDNA sequences, etc.

The present invention also provides primers prepared from SEQ ID No. 1 that can be used to locate and identify homologs and orthologs in any prokaryotic or eukaryotic organism. The present invention also provides methods of using such primers to obtain and isolate such homologs and orthologs to SEQ ID No. 1.

The present invention also provides methods of using all or part of the sequence of SEQ ID No. 1 to identify homologs or orthologs by searching nucleic acid sequence data bases. Examples of such databases include but are not limited to the genomic sequence databases for corn, rice and *Arabidopsis*. Such sequence searching methods are well know to those skilled in the art.

The present invention also provides any nucleic acid sequences that hybridize to SEQ ID No. 1 under stringent conditions. Such conditions are well known to those practiced in the art, using methods taught by, for example, Sambrook et al (1989), but are normally a combination of temperature and salt concentration that is approximately 20 degrees Celsius below the calculated melting temperature ($T_m$) of the target molecule. The melting temperature is typically calculated using the formula of Bolton and McCarthy (1962).

The present invention further provides isolated nucleic acid molecules and their complements that encode a sequence with at least about 65% sequence identity to SEQ ID No. 1, or at least about 70% sequence identity, or at least about 75% sequence identify, or at least about 80% sequence identity, or at least about 85% sequence identity, or at least about 86% sequence identity, or at least about 87% sequence identity, or at least about 88% sequence identity, or at least about 89% sequence identity, or at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity, or at least about 99.5% sequence identity, or at least about 99.9% sequence identity with SEQ ID No. 1. The present invention also provides any such nucleic acids which encode a peptide or protein with BOMB activity.

The present invention further provides isolated amino acids that encode a sequence with at least about 65% sequence identity to SEQ ID No. 2, or at least about 70% sequence identity, or at least about 75% sequence identify, or at least about 80% sequence identity, or at least about 85% sequence identity, or at least about 86% sequence identity, or at least about 87% sequence identity, or at least about 88% sequence identity, or at least about 89% sequence identity, or at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity, or at least about 99.5% sequence identity, or at least about 99.9% sequence identity with SEQ ID No. 2. The present invention also provides the peptides and proteins encoded by such amino acid sequences including those with BOMB activity.

The invention also provides a DNA coding region of claim 2, consisting of bombBC (SEQ ID No. 1) or any DNA sequence consisting of a stretch of 70% DNA sequence identity over a stretch of 50 base pairs. This is a practical standard that is used by the Food Allergy Research Resource Program to determine if a protein is likely to be similar to any known allergens, based either on protein or DNA coding sequences.

The invention also provides a peptide fragment consisting of at least 8 contiguous amino acids of BombBC (SEQ ID No. 2), OR any peptide fragment or protein having 35% or greater similarity over 80 amino acids with BombBC (SEQ ID No. 2). This is a practical standard that is used by the Food Allergy Research Resource Program to determine if a protein is likely to be similar to any known allergens, based either on protein or DNA coding sequences.

The present invention provides an isolated nucleic acid sequence comprising, consisting essentially of, or consisting of a nucleic acid sequence of SEQ ID No. 1 and conservative substitutions thereof; a nucleic acid sequence with at least 70% nucleic acid sequence identity to SEQ ID No. 1; a contiguous nucleic acid sequence with at least 70% nucleic acid sequence identity to a contiguous nucleic acid sequence of at least 50 base pairs of SEQ ID No. 1; a nucleic acid sequence which hybridizes to the nucleic acid sequence of SEQ ID No. 1 under stringent hybridization conditions; or encodes the amino acid sequence of SEQ ID No. 2. The present invention also provides nucleic acid constructs, vectors, plant cells, plant parts, plant tissues and whole plants comprising such nucleic acid sequences. The plant can be any plant, such as any monocotyledonous plant or any dicotyledonous plant. Examples of such plants useful in the present invention include but are not limited to a geranium, tobacco, citrus and rice. The present invention also provides methods of transforming a plant cell comprising introducing into the plant cell the isolated nucleic acid sequences of the present invention.

The present invention may also find use in transforming or treating algae for bacterial infections, including by transforming algae with the sequences provided by the present invention.

The present invention also provides methods for enhancing the resistance of a plant to infection or infestation by Gram-negative bacteria, whether pathogenic or not, comprising introducing into the plant genome of said plant the nucleic acid sequences of the present invention.

The present invention also provides isolated peptides, polypeptides or proteins comprising, consisting essentially of, or consisting of an amino acid sequence of SEQ ID No. 2; an amino nucleic acid sequence with at least 8 contiguous amino acids of SEQ ID No. 2; an amino acid sequence which hybridizes to the amino acid sequence of SEQ ID No. 2 under stringent hybridization conditions; or an amino acid sequence having 35% or greater amino acid sequence similarity over at least 80 amino acids with the amino acid sequence of SEQ ID No. 2.

The present invention also provides isolated peptides, polypeptides or proteins which are derived from a bacteriophage; lack a bacterial secretion signal amino acid sequence; lack a transmembrane domain; that when expressed in a bacterium, does not cause lysis, but instead causes "quasilysis", whereby the optical density of the culture increases shortly after induction and thereafter declines to approximately the starting optical density; and that when expressed in a bacterium grown in the presence of a phytoalexin, it causes "quasilysis" and additional cell death, whereby the optical density of the culture increases shortly after induction and thereafter declines a level significantly below that of the starting optical density.

The plant cells, plant parts, plant tissues or whole plants of the present invention can also cause insects and nematodes to fail to thrive or to avoid feeding on said plant cell, plant part, plant tissue or whole plant due to inhibition or killing of symbiotic Gram-negative bacteria that are important for digestion or survival of the insect or nematode.

The present invention also provides methods of preventing, treating or reducing a Gram-negative bacterial infection or infestation of a plant cell, plant part, plant tissue or whole plant, said method comprising contacting the plant cell, plant part, plant tissue, or whole plant with the isolated peptide, polypeptide or protein of the present invention.

The present invention also provides compositions comprising the isolated peptides, polypeptides or proteins of the present invention. Examples of such compositions include but are not limited to seed treatments, such as seed coatings, and other forms of such compositions including but not limited to sprays, powders, slurries, dustings and the like.

The present invention provides methods of preventing, treating or reducing microbial infection of an animal cell, animal tissue, or whole animal, said method comprising contacting the animal cell, animal tissue, or whole animal with the isolated peptides, polypeptides or proteins of the present invention. The peptides, polypeptides or proteins may be included in compositions used to treat such animals. Examples of such compositions include but are not limited to sprays, powders, slurries, patches, implants and the like.

The present invention provides methods of preventing, treating or reducing microbial infection of a surface or device, such as a countertop used to prepare food or a medical device, said methods comprising contacting the surface or device with the isolated peptides, polypeptides or proteins of the present invention. The peptides, polypeptides or proteins may be included in compositions used to treat such surfaces and devices. Examples of such compositions include but are not limited to paints, detergents, sprays, powders, slurries, patches, implants and the like.

The present invention provides methods for enhancing the resistance of a plant cell, plant part, plant tissue or whole plant to infection or infestation by Gram-negative bacteria comprising introducing into the plant cell, plant part, plant tissue or whole plant an expression cassette comprising as operably linked components: a) a promoter region functional in plants; b) a nucleic acid sequence of claim 1, claim 2 or claim 3; and c) a terminator region functional in plants; and then allowing expression of the expression cassette; thereby obtaining enhanced resistance of the plant cell, plant part, plant tissue or whole plant to infection or infestation by Gram-negative bacteria. Such methods can further comprise self-pollinating the whole plants with the introduced expression cassette or cross-pollinating the whole plants with the introduced expression cassette to a plant of its same species. In addition, such methods can even further comprise testing the whole plants obtained by introducing the expression cassette for the presence of the expression cassette or enhanced resistance to infection or infestation by Gram-negative bacteria prior to self- or cross-pollinating the whole plants. The methods can further comprise harvesting any seeds produced as a result of the self- or cross-pollinations. Such methods can even further comprise germinating the harvested seeds to produced seedlings and testing plant cells, plant parts, plant tissues or whole plants of the germinated seedlings for the presence of the expression cassette or enhanced resistance to infection or infestation by Gram-negative bacteria.

The present invention also provides tissue cultures of the plant cells, plant parts, plant tissues or whole plants obtained by the methods of the present invention, wherein the so obtained plant cells, plant parts, plant tissues or whole plants contain the introduced expression cassette.

The whole plants obtained according to the methods of the present invention which contain the introduced nucleic acid sequences can further be self- or cross-pollinated to another plant of the same species. Any resultant seeds can be harvested and used to produce further plants for self- and cross-pollination.

The methods of the present invention can be used for both pathogenic and non-pathogenic Gram-negative bacteria.

The methods of the present invention can further comprise introducing into the plant genome a second nucleic acid sequence coding for a second peptide, polypeptide or peptide which enhances the resistance of the plant to infection or infestation by a plant pathogen. The second peptide, polypeptide or protein can include but not be limited to a nonenzymatic lytic peptide, an enzymatic lytic peptide, or an enzymatic peptidoglycan degrading peptide. For example, the second peptide, polypeptide or protein can be a lysozyme, an endolysin, a protease, a mureinolytic enzyme, an enzyme with transglycosylase activity, a lipase and an esterase.

DETAILED DESCRIPTION

Figure 1:
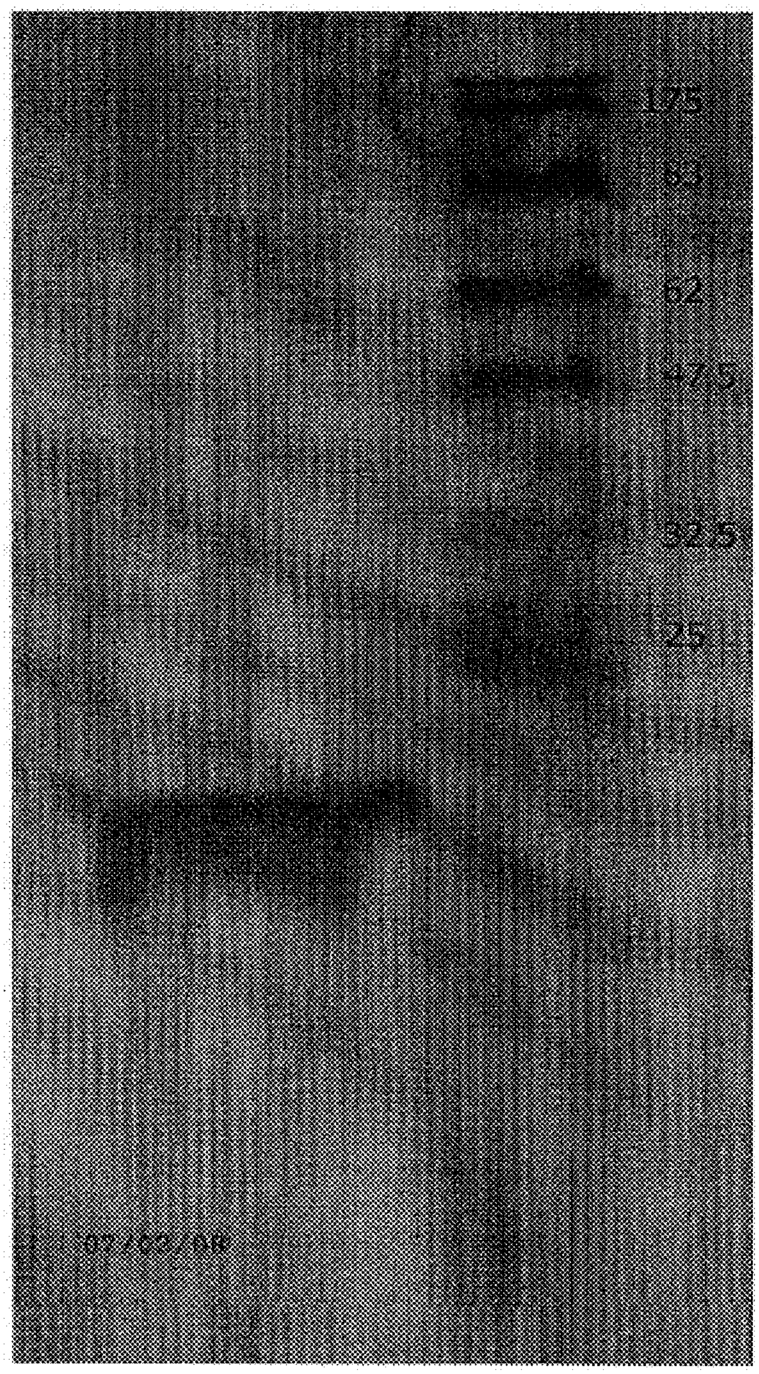
FIG. 1 shows purified BombBC protein (18 kDa) in lane 1 and molecular weight markers of indicated size in lane 2 of a polyacrylamide gel stained with Coomassie blue.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described. The DNA cloning techniques used in the present invention are conventional and can be performed by anyone skilled in the art, using methods taught by, for example, Sambrook et al (1989).

The present invention is based on our discovery that at least some bacteriophage encode previously unknown proteins called BOMB (Bacterial Outer Membrane Breaching) proteins that strongly inhibit growth of at least some bacteria in culture, evidently by degrading or affecting the structure of the LPS barrier of the bacteria. Furthermore, we discovered that: 1) surfactants, 2) enzymes that attack the peptidoglycan or cell wall, and 3) plant defense compounds increase the efficacy of expressed BOMBs against culture grown Gram-negative. Furthermore, we discovered that BombBC, from bacteriophage Xp15 of *X. pelargonii*, had a lethal or inhibitory effect on multiple Gram-negative bacteria when expressed in various different transgenic plants, both monocots and dicots. Finally, we discovered that not only can at least some BOMBs, such as BombBC, be stably produced by plant cells without toxic effects to plants, but that said expression of BOMB genes in plants provides a novel means of protecting plants against Gram-negative bacteria.

The present invention is also based on our discovery that at least some plant secretion signal peptides may be used as a means for targeting the antimicrobial effect of BOMBs to the plant apoplast and xylem, where they accumulate, providing a novel means of protecting plants against a wide variety of gram negative bacteria. Furthermore, we have discovered that transgenic plants expressing BOMBs may be used to produce crude or purified extracts of antimicrobial compounds.

The following exemplary embodiments are intended to illustrate the present invention in greater detail:

1. To identify BOMB and/or BOMB-like genes, it is first necessary to isolate and purify a DNA bacteriophage that has very strong antimicrobial activity against a variety of target organisms. This is accomplished by first obtaining bacteriophage that attack target Gram negative bacteria. Bacteriophage that attack a specific bacterium may be isolated with ease from raw sewage, pond water, or drainage from greenhouse complexes using well publicized methods known to those skilled in the art. Secondly, a variety of bacteriophage plaques are evaluated by size of the plaques formed after plating the bacteriophage with a gram negative host bacterium using methods known to those skilled in the art. Thirdly, bacteriophage are selected by their ability to lyse or inhibit additional gram negative bacteria that they are incapable of infecting. This is accomplished by a series of infection assays and overlay assays. Finally, phage nucleic acid is isolated and treated with DNAse and separately with RNAse using methods known to those skilled in the art. Only DNA based phage are selected.

2. Following phage purification, the bacteriophage DNA is fragmented and fully sequenced, as exemplified by Phage 15 sequence deposited in GenBank as Accession NC_007024. There are a variety of strategies available for this purpose known to those skilled in the art; sequencing may be accomplished by shot-gun library sequencing or by subcloning, restriction mapping and sequencing using primer walking techniques. Phage genomic regions expressing BOMBs from gram negative bacteria may not be readily clonable in *E. coli* and are recognized by the fact that they can only be cloned either without their native promoters or cloned downstream of fully repressed promoters. These regions may be sequenced directly from phage DNA.

3. Following DNA sequencing of the bacteriophage genome, transcriptional direction is determined by identification of promoters and transcriptional terminators using programs well known to those skilled in the art. Phage genomes are typically transcribed as polycistronic messages in large blocks. All open reading frames (ORFs) are then identified using programs well known to those skilled in the art, and likely functional genes (LFGs) are also identified, based on length of the ORF, codon usage, third position codon bias, presence or absence of Shine-Delgarno sequences and transcriptional context, including likely promoters, transcriptional terminators and direction of transcription. The biochemical functions of some of the LFGs are then determined by comparisons with other, often characterized genes catalogued in large databases such as GenBank®. Since BOMBs have not previously been described, the BOMB genes are unlikely to be discovered by comparisons with any known genes in public or private databases.

4. The genes encoding BOMBs and/or BOMB-like genes are identified by examining every LFG of the phage, starting with those found in any DNA fragment that is not sub-clonable. BOMB characteristically are: 1) small (20 kD or less) LFGs with 2) multiple helix-loop-helix-loop domains, 3) no transmembrane domains and 4) no leader sequences. LFGs with these characteristics are then selected for further testing using a functional gene expression assay. The predicted peptide coding regions of the putative BOMB genes are amplified by polymerase chain reaction (PCR) from the phage DNA and cloned without promoters in a suitable vector. These coding regions are then operably fused with strongly regulated, repressible promoters in suitable bacterial expression vectors. Repression of the promoter operably fused with the putative BOMB genes is then released, which should result in a noticeable reduction or termination of growth of the *E. coli* strains carrying the clones. Any such clones are then further tested for their effect on other bacteria.

5. Any DNA clones that, on induction, cause a noticeable reduction or termination of growth of the *E. coli* strains carrying the clones are further evaluated by measuring the optical density OD at 600 nanometers (nm) of the cultures over a 24 hour period of time starting with a low, but measurable OD at the time of induction. These measurements are taken in the presence and in the absence of a phytoalexin such as berberine or a detergent such as Silwet L77. Observations are made for evidence of cell lysis or lack thereof. Any DNA clones that, upon induction, cause a continuous decline in cell density over time (up to 24 hrs) are likely BOMB candidate genes. Such clones may be further confirmed as BOMB genes if the effect of added phytoalexin, such as berberine chloride, or wetting agent, such as Silwet L77 is synergistic with the DNA clone in reducing cell culture density continuously over time (up to 24 hrs). In one embodiment is a cloned bombBC.

6. Said BOMB clone is operably fused within a plant gene expression cassette, minimally comprising a promoter that is functional in plants, followed by the BOMB clone and followed by a plant terminator in a plant expression vector that may be used for transient gene expression in plants. Several plant promoters and promoters from plant viruses that are functional in plants are widely available for use to functionally express a foreign gene in plants in transient expression assays, for example, the CaMV promoter found in the pCAMBIA series of plant expression vectors (Cambia, Can berra, Australia). Several plant terminators are also available, including the widely available NOS terminator, also found in the pCAMBIA plant expression vector series. For transfer into plant cells, the plant expression vectors may optionally also contain T-DNA borders and ability to replicate in *Agrobacterium tumefaciens, Rifizobium* spp., *Sinorifizobium* spp. or *Mesorifizobium* spp., which are subsequently used to transfer the DNA region between the T-DNA borders into plants.

7. In another embodiment, an intron may be optionally used to increase gene expression. Introns are known to be required for abundant expression of many genes in plants, including both dicots and ornamental plants and especially monocots, possibly by enhancing transcript stability or facilitating mRNA maturation (Callis et al., 1987; Mun, J. H. et al. 2002; Rose & Beliakoff, 2000; Rose, 2002, Simpson & Filipowicz, 1996).

8. In one embodiment, a plant secretion signal is added to the BOMB coding region. Some plant stress-associated and/or disease-associated proteins have been found to accumulate preferentially and most abundantly in the xylem of plants, presumably requiring a specific secretion signal sequence. Only a very few proteins are found in the xylem; it is unclear how they are secreted through the plant cell wall to reach the xylem. Such proteins have secretion signal peptides that are useful for targeting antimicrobial compounds to the plant apoplast and xylem; we call these "xylem secretion signal peptides". The xylem secretion signal peptide sequence is amplified from an appropriate plant source by PCR and cloned upstream of the BOMB sequence. One embodiment is a 24 amino acid plant signal peptide derived from one such protein, P12 (GenBank Accession #AF015782; Ceccardi et al., 1998).

9. Plant expression of an active, correctly folded BOMB is verified in any one of several plant species using transient gene expression (Wroblewski et al. 2005). The plant expression vector carrying the BOMB gene cloned in the gene expression cassette is transformed into *A. tumefaciens*, and the resulting transformed cells are inoculated into plants by flooding a sizeable area of leaf tissue with diluted cell cultures. An empty vector control, consisting of the plant expression vector but without the BOMB gene cloned in the expression cassette, is also inoculated, preferably on the same leaf. After 3-4 days, protein is extracted from the plant tissue that has been inoculated and used for Western blot analysis. BOMB protein levels in the tissues inoculated with the BOMB clone are compared with BOMB levels in the tissues inoculated with the empty vector control.

10. The most active DNA constructs are then tested in host plant transient expression challenge assays using appropriate pathogenic species of Gram negative bacteria; for example, *Xanthomonas* pelargonii inoculated into geranium or *Ralstoma solanacearum* inoculated into tobacco, geranium, tomato or pepper. Nonhost plant transient expression challenge assays may also be used, provided the nonhost plant produces a visible hypersensitive response (HR) to the challenge pathogen. In both cases, plant leaf tissues are inoculated by flooding with diluted cultures of *A. tumefaciens* carrying the BOMB gene expression vector exactly as illustrated in embodiment 5, above, and the extent of the inoculated areas is marked. After 3-4 days, the plant tissue that has been inoculated is again super-inoculated in the same tissue zone, this time with a plant pathogen or target Gram-negative bacterium that has an antibiotic resistance marker different from that of the *A. tumefaciens* strain used. If a pathogen, visible pathogenic symptoms or the HR response observed on the empty vector control tissues is compared that observed with the BOMB clone tissues. Whether pathogen or nonpathogen, 1 cm leaf disks are removed from within the super-inoculated zones, ground in medium and cell count assays are performed, comparing cell counts from zones inoculated within the empty vector control tissues with those taken from zones inoculated with the BOMB clone.

11. Permanent transformation of plant cells, both monocots and dicots, followed by regeneration and propagation of transformed plants of the desired dicot and monocot species of interest are then undertaken.

It is also an object of the invention to prevent diseases of both monocot and dicot plants prophylactically by killing any Gram-negative bacterium that infects or feeds on the plant and causes plant disease. In one embodiment of the invention, the prophylactic and therapeutic treatment of a variety of diseases caused by various species and pathovars of *Xanthomonas, Pseudomonas, Erwinia, Agrobacterium*, Ca. Liberibacter, *Xylella, Ralstoma* and *Burkholderia* is achieved. Transgenic plants are created using plants that are hosts of the indicated pathogen genus, said host plants carrying one or more BOMB, or BOMB-like peptides fused with a xylem secretion signal peptide, operably linked with a plant promoter such that the BOMB-like peptides are made by the plants.

It is also an object of the invention to prevent food-borne diseases of humans and animals in both monocot and dicot plants by prophylactically killing any Gram-negative bacterium that infects or feeds on the plant and causes a food-borne disease of humans and/or animals. In one embodiment of the invention, the prophylactic and therapeutic elimination of fecal bacteria that can infect fresh vegetables such as spinach and bean sprouts and cause a variety of intestinal diseases, including *Escherichia, Shigella* and *Salmonella* is achieved. Transgenic plants are created using plants that are hosts of the indicated pathogen genus, said host plants carrying one or more BOMB or BOMB-like peptides fused with a xylem secretion signal peptide, operably linked with a plant promoter such that the BOMB-like peptides are made by the plants.

In another embodiment of the invention, transgenic plants are created that are hosts of the indicated genus, said host plants carrying one or more BOMB or BOMB-like peptides fused with a xylem secretions signal peptide together with an esterase, a lytic peptide or lytic enzyme, all operably linked with plant promoters such that the BOMB and/or BOMB-like peptides and lytic enzymes are made by the plant hosts. Lytic peptides or enzymes may be linear or compact and globular, and include but are not limited to lysozymes, cecropins, attacins, magainins, holins, permeability increasing proteins, etc.

It is a further object of the invention to prevent or to dampen epidemics or plagues by planting these transgenic plants as "trap" plants in an environment such that populations of infectious bacteria, fungi, nematodes or insects are reduced by feeding upon the transgenic plants. Such an environment may include commercial crops, including nontransgenic crops of the same or different plant species as the transgenic trap plants, gardens and inside buildings.

It is also an object of the invention to prophylactically prevent contamination of livestock feed and human foods by killing any Gram negative bacterium that might contaminate the feed or foods. In another embodiment of the invention, livestock feeds may incorporate or consist of transgenic whole plants, transgenic plant parts or a crude, semi-pure or pure extract of transgenic plants expressing BOMB and/or BOMB-like enzymes or peptide fragments. In another embodiment of the invention, human foods such as eggs or sprouts may be treated with a spray preparation of BOMBs and or BOMB-like enzymes or peptide fragments made from transgenic plants.

DEFINITIONS

As used herein, the term "BOMB" refers inclusively to any bacteriophage derived protein: 1) without a bacterial secretion signal sequence; 2) without a transmembrane domain, and 3) with the capacity to negatively affect, breach, permeabilize or degrade the outer LPS barrier of Gram negative bacteria. Expression of a BOMB protein in *E. coli* causes "quasilysis"—upon induction, the optical density of the cell culture continues to increase for one to two hours in a manner similar to that of an uninduced culture, but then the optical density drops back to the starting level at the time of induction. BOMBs lack the capacity to cause lysis—upon induction, the optical density of the cell culture drops abruptly. BOMBs also lack the capacity to disrupt the inner membrane of bacteria in a manner similar to that of holins when produced or overproduced inside a bacterial cell. Disruption of the inner membrane of a bacterium is assayed by expression of both a BOMB gene and an endolysin gene simultaneously inside a bacterial cell; over-expression of a BOMB gene and endolysin simultaneously will not result in cell lysis within several hours or less.

As used herein, the term "holin" refers to any bacteriophage derived protein with at least one transmembrane domain with the capacity to disrupt the inner membrane of bacteria when produced without a leader inside a bacterial cell. Disruption of the inner membrane of a bacterium is assayed by expression of both the holin gene and an endolysin gene simultaneously inside a bacterial cell; over-expression of a holin gene and endolysin simultaneously will result in cell lysis within several hours or less.

As used herein, the term "endolysin" refers to any enzyme capable of depolymerization of the murein or peptidoglycan cell wall. The term includes: 1) glucosaminidases (lysozymes) that attack the glycosidic linkages between the amino sugars of the peptidoglycan; 2) amidases that attack the N-acetylmuramoyl-L-alanine amide linkage between the glycan strand and the cross-linking peptide, and 3) endopeptidases that attack the interpeptide bridge linkages (Sheehan et al., 1997). Endolysins are synthesized without an export signal sequence that would permit them access to the peptidoglycan (murein) layer, and they therefore usually accumulate in the cytoplasm of phage infected bacteria until they are released by the activity of holins.

As used herein, the term "quasilysis" means that upon induction, the optical density of the cell culture continues to increase for one to two hours in a manner similar to that of an uninduced culture, but then the optical density drops back to the starting level at the time of induction.

As used herein, the term "lysis" means that upon induction, the optical density of the cell culture drops abruptly.

As used herein, the term "esterase" refers inclusively to any enzyme categorized as either a carboxylic-ester hydrolase (EC 3.1.1.1) or a triacylglycerol acylhydrolase (EC 3.1.1.3).

As used herein, the term "carboxylic-ester hydrolase" (EC 3.1.1.1), refers to a "carboxylesterase" and catalyzes the reaction of a carboxylic ester+$H_2O$ to an alcohol plus a carboxylate. Other common names for carboxylic-ester hydrolase are: ali-esterase; B-esterase; monobutyrase; cocaine esterase; procaine esterase; methylbutyrase; vitamin A esterase; butyryl esterase; carboxyesterase; carboxylate esterase; carboxylic esterase; methylbutyrate esterase; triacetin esterase; carboxyl ester hydrolase; butyrate esterase; methylbutyrase; carboxylesterase; propionyl esterase; nonspecific carboxylesterase; esterase D; esterase B; esterase A; serine esterase; carboxylic acid esterase; cocaine esterase.

As used herein, the term "lipase" refers to any triacylglycerol acylhydrolase (EC 3.1.1.3), commonly called "triacylglycerol lipase" and catalyzing the reaction of triacylglycerol plus $H_2O$ to diacylglycerol plus a carboxylate. Other common names for lipase are: tributyrase; butyrinase; glycerol ester hydrolase; tributyrinase; Tween hydrolase; steapsin; triacetinase; tributyrin esterase; Tweenase; amno N-AP; Takedo 1969-4-9; Meito MY 30; Tween esterase; GA 56; capalase L; triglyceride hydrolase; triolein hydrolase; tween-hydrolyzing esterase; amano CE; cacordase; triglyceridase; triacylglycerol ester hydrolase; amano P; amano AP; PPL; glycerol-ester hydrolase; GEH; meito Sangyo OF lipase; hepatic lipase; lipazin; post-heparin plasma protamine-resistant lipase; salt-resistant post-heparin lipase; heparin releasable hepatic lipase; amano CES; amano B; tributyrase; triglyceride lipase; liver lipase; hepatic monoacylglycerol acyltransferase.

As used herein, the term "Gram-negative bacterium" refers to any bacterium producing lipopolysaccharide (LPS).

As used herein, the term "disease resistance" refers to any reduction in disease symptoms or pathogen numbers in the plant or material tested caused by the treatment, as compared with the most susceptible phenotypic symptoms or pathogen numbers known in comparable tests of untreated plants or materials.

As used herein, the term "resistance" to bacteria refers to any reduction in bacterial numbers in the plant or material tested caused by the treatment, as compared with untreated plants or materials.

As used herein, the term "immunity" to bacteria refers to elimination of detectable bacterial cell counts in the plant or material tested caused by the treatment, as compared with untreated plants or materials.

As used herein, the term "allele" refers to any of several alternative forms of a gene.

As used herein, the term "amino acid" refers to the aminocarboxylic acids that are components of proteins and peptides. The amino acid abbreviations are as follows: A (Ala); C (Cys); D (Asp); E (Glu); F (Phe); G (Gly); H (His); I (Iso); K (Lys); L (Leu); M (Met); N (Asn); P (Pro); Q (Gin); R (Arg); S (Ser); T (Thr); V (Val); W (Trp), and Y (Tyr).

As used herein, "Homologous" refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity." In addition, when the terms "homology" or "identity" are used herein to refer to the nucleic acids and proteins, it should be construed to be applied to homology or identity at both the nucleic acid and the amino acid sequence levels. A first oligonucleotide anneals with a second oligonucleotide with "high stringency" or "under high stringency conditions" if the two oligonucleotides anneal under conditions whereby only oligonucleotides which are at least about 60%, more preferably at least about 65%, even more preferably at least about 70%, yet more preferably at least about 80%, and preferably at least about 90% or, more preferably, at least about 95% complementary anneal with one another. The stringency of conditions used to anneal two oligonucleotides is a function of, among other factors, temperature, ionic strength of the annealing medium, the incubation period, the length of the oligonucleotides, the G-C content of the oligonucleotides, and the expected degree of non-homology between the two oligonucleotides, if known. Methods of adjusting the stringency of annealing conditions are known (see, e.g., Sambrook et al., 1989, In: Molecular Cloning: A Laboratory Manual, Cold Spring Harbor Laboratory, New York).

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul et al. (1990, J. Mol. Biol. 215:403-410), and can be accessed, for example, at the BLAST site of the National Center for Biotechnology Information (NCBI) world wide web site at the National Library of Medicine (NLM) at the National Institutes of Health (NIH). BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein.

To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (id.) and relationships between molecules which share a common pattern. When utilizing BLAST, Gapped BLAST, PSI-Blast, and PHI-Blast programs, the default parameters of the respective programs (e.g., XBLAST and NBLAST) can be used as available on the website of the National Center for Biotechnology Information of the National Library of Medicine at the National Institutes of Health.

The percent identity between two sequences can be determined using techniques similar to those described above, with or without allowing gaps. In calculating percent identity, typically exact matches are counted.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

As used herein, the term "crop plant" refers to any plant grown for any commercial purpose, including, but not limited to the following purposes: seed production, hay production, ornamental use, fruit production, berry production, vegetable production, oil production, protein production, forage production, animal grazing, golf courses, lawns, flower production, landscaping, erosion control, green manure, improving soil tilth/health, producing pharmaceutical products/drugs, producing food or food additives, smoking products, pulp production and wood production.

As used herein, the term "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include citrus; geranium; tobacco; tomato; the legumes, including peas, alfalfa, clover and soybeans; oaks; maples; roses; mints; squashes; daisies; walnuts; cacti; violets and buttercups.

As used herein, the term "ER retention signal" refers to an amino acid sequence (the ER retention signal peptide) attached to a polypeptide which causes the polypeptide to be retained and accumulated in the endoplasmic reticulum (ER).

As used herein, the term "female plant" refers to a plant that produces ovules. Female plants generally produce seeds after fertilization. A plant designated as a "female plant" may contain both male and female sexual organs. Alternatively, the "female plant" may only contain female sexual organs either naturally (e.g., in dioecious species) or due to emasculation (e.g., by detasselling).

As used herein, the term "filial generation" refers to any of the generations of cells, tissues or organisms following a particular parental generation. The generation resulting from a mating of the parents is the first filial generation (designated as "F1" or "$F_1$"), while that resulting from crossing of F1 individuals is the second filial generation (designated as "F2" or "$F_2$").

As used herein, the term "gamete" refers to a reproductive cell whose nucleus (and often cytoplasm) fuses with that of another gamete of similar origin but of opposite sex to form a zygote, which has the potential to develop into a new individual. Gametes are haploid and are differentiated into male and female.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the term "lytic protein" refers to any enzyme, in whole or in part, or lytic peptide that: 1) degrades or penetrates the peptidoglycan or murein layer that forms the bacterial cell wall of both Gram positive or Gram negative bacteria, and 2) has the ability to permeabilize or disrupt the bacterial inner membrane. Said proteins may be linear, partially degraded or compact and globular, and include but are not limited to lysozymes, cecropins, attacins, magainins, permeability increasing proteins, etc.

As used herein, the term "male plant" refers to a plant that produces pollen grains. The "male plant" generally refers to the sex that produces gametes for fertilizing ova. A plant designated as a "male plant" may contain both male and female sexual organs. Alternatively, the "male plant" may only contain male sexual organs either naturally (e.g., in dioecious species) or due to emasculation (e.g., by removing the ovary).

As used herein, the term "mass selection" refers to a form of selection in which individual plants are selected and the next generation propagated from the aggregate of their seeds.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the terms "mutant" or "mutation" refer to a gene, cell, or organism with an abnormal genetic constitution that may result in a variant phenotype.

As used herein, the terms "nucleic acid" or "polynucleotide" refer to deoxyribonucleotides or ribonucleotides and polymers thereof in either single- or double-stranded form. Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucleic Acid Res. 19:5081; Ohtsuka et al. (1985) J. Biol. Chem. 260:2605-2608; Cassol et al. (1992); Rossolini et al. (1994) Mol. Cell. Probes 8:91-98). The term nucleic acid is used interchangeably with gene, cDNA, and mRNA encoded by a gene. The term "nucleic acid" also encompasses polynucleotides synthesized in a laboratory using procedures well known to those skilled in the art.

As used herein, a DNA segment is referred to as "operably linked" when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Generally, DNA sequences that are operably linked are contiguous, and in the case of a signal sequence both contiguous and in reading phase. However, enhancers need not be contiguous with the coding sequences whose transcription they control. Linking is accomplished by ligation at convenient restriction sites or at adapters or linkers inserted in lieu thereof.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein, the terms "ortholog" and "orthologue" refer to a nucleic acid or peptide sequence which functions similarly to a nucleic acid or peptide sequence from another species. For example, where one gene from one plant species has a high nucleic acid sequence similarity and codes for a protein with a similar function to another gene from another plant species, such genes would be orthologs.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "phytoalexin" refers to any antimicrobial chemical compound made by a plant, whether preformed or made in response to presence of a microbe.

As used herein, the term "plant line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses effected such that a gene or a combination of genes, in heterozygous (hemizygous) or homozygous condition, imparts a desired trait to the plant.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "promoter" refers to a region of DNA involved in binding RNA polymerase to initiate transcription.

As used herein, the terms "protein," "peptide" or polypeptide" refer to amino acid residues and polymers thereof. Unless specifically limited, the terms encompass amino acids containing known analogues of natural amino acid residues that have similar binding properties as the reference amino acid and are metabolized in a manner similar to naturally occurring amino acid residues. Unless otherwise indicated, a particular amino acid sequence also implicitly encompasses conservatively modified variants thereof (e.g. conservative substitutions) as well as the sequence explicitly indicated. The term "polypeptide" also encompasses polypeptides synthesized in a laboratory using procedures well known to those skilled in the art.

As used herein, the term "recombinant" refers to a cell, tissue or organism that has undergone transformation with recombinant DNA. The original recombinant is designated as "R0" or "$R_0$." Selfing the R0 produces a first transformed generation designated as "R1" or "$R_1$."

As used herein, the term "secretion signal" refers to an amino acid sequence (the secretion signal peptide) attached to a N-terminus of a polypeptide, which is needed for secretion of the mature polypeptide from the cell.

As used herein, the term "self pollinated" or "self-pollination" means the pollen of one flower on one plant is applied (artificially or naturally) to the ovule (stigma) of the same or a different flower on the same plant.

As used herein, the term "transcript" refers to a product of a transcription process.

As used herein, the term "transformation" refers to the transfer of nucleic acid (i.e., a nucleotide polymer) into a cell.

As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, the term "transposition event" refers to the movement of a transposon from a donor site to a target site.

As used herein, the term "variety" refers to a subdivision of a species, consisting of a group of individuals within the species that are distinct in form or function from other similar arrays of individuals.

As used herein, the terms "untranslated region" or "UTR" refer to any part of a mRNA molecule not coding for a protein (e.g., in eukaryotes the poly(A) tail).

As used herein, the term "vector" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

Plant Transformation

As discussed herein, several embodiments of the present invention employ expression units (or expression vectors or systems) to express an exogenously supplied nucleic acid sequence in a plant. Methods for generating expression units/systems/vectors for use in plants are well known in the art and can readily be adapted for use in the instant invention. A skilled artisan can readily use any appropriate plant/vector/expression system in the present methods following the outline provided herein.

The expression control elements used to regulate the expression of the protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefacians*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as RUBISCO small and large subunit promoters, prolifera promoter, fruit-specific promoters, Ap3 promoter, heat shock promoters, seed-specific promoters, etc. can also be used.

Either a gamete-specific promoter, a constitutive promoter (such as the CaMV or Nos promoter), an organ-specific promoter (such as the E8 promoter from tomato) or an inducible promoter is typically ligated to the protein or antisense encoding region using standard techniques known in the art. The expression unit may be further optimized by employing supplemental elements such as transcription terminators and/or enhancer elements.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO *j* 3:835-846 (1984)) or the nopaline synthase signal (Depicker et al., Mol. and Appl. Genet. 1:561-573 (1982)).

The resulting expression unit is ligated into or otherwise constructed to be included in a vector that is appropriate for higher plant transformation. The vector may also contain a selectable marker gene by which transformed plant cells can be identified in culture. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as ampicillin, kanamycin or tetracycline.

Other DNA sequences encoding additional functions may also be present in the vector, as is known in the art. For instance, in the case of *Agrobacterium, Rhizobium, Mesorhizobium* and *Sinorhizobium* transformations, T-DNA sequences will also be included for subsequent transfer to plant chromosomes.

The sequences of the present invention can also be fused to various other nucleic acid molecules such as Expressed Sequence Tags (ESTs), epitopes or fluorescent protein markers.

ESTs are gene fragments, typically 300 to 400 nucleotides in length, sequenced from the 3' or 5' end of complementary-DNA (cDNA) clones. Nearly 30,000 *Arabidopsis thaliana* ESTs have been produced by a French and an American consortium (Delseny et al., FEBS Lett. 405(2):129-132 (1997); *Arabidopsis thaliana* Database). For a discussion of the analysis of gene-expression patterns derived from large EST databases, see, e.g., M. R. Fannon, TIBTECH 14:294-298 (1996).

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; *Agrobacterium*-, *Rhizobium*-, *Mesorhizobium*- and *Sinorffizobium*-mediated transformation. See, for example, U.S. Pat. Nos. 5,405,765; 5,472,869; 5,538,877; 5,538,880; 5,550,318; 5,641,664; 5,736,369; 5,736369; US 2005/0289672; US 2005/0289667, PCT Publication WO 2006/004914; Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); Raineri et al., Bio/Tech. 8:33-38 (1990), and Broothaerts et al., Nature 433:629-633 (2005), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. It can also insert foreign DNA into plants through the use of its modified or "disarmed" natural DNA insertion system, but without forming crown gall disease. Most species of plants can now be transformed using this method. See, for example, Wang et al., Australian journal of Plant Physiology 23(3): 265-270 (1996); Hoffman et al., Molecular Plant-Microbe Interactions 10(3): 307-315 (1997); and, Trieu et al., Plant Cell Reports 16:6-11 (1996).

*Rhizobium* spp., *Mesorhizobium* spp. and *Sinorhizobium* spp. are naturally occurring bacteria that are also capable of inserting foreign DNA (genetic information) into plants. Many species of plants can now be transformed using this method. See, for example, Broothaerts et al., Nature 433:629-633 (2005).

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method, including alfalfa (U.S. Pat. No. 5,324,646) and clover (Voisey et al., Biocontrol Science and Technology 4(4): 475-481 (1994); Quesbenberry et al., Crop Science 36(4): 1045-1048 (1996); Khan et al., Plant Physiology 105 (1): 81-88 (1994); and, Voisey et al., Plant Cell Reports 13(6): 309-314 (1994)).

Developed by ICI Seeds Inc. (Garst Seed Company) in 1993, WHISKERS' is an alternative to other methods of inserting DNA into plant cells (e.g., the Biolistic® Gene Gun, *Agrobacterium tumefaciens*, the "Shotgun" Method, etc.); and it consists of needle-like crystals ("whiskers") of silicon carbide. The fibers are placed into a container along with the plant cells, then mixed at high speed, which causes the crystals to pierce the plant cell walls with microscopic "holes" (passages). Then the new DNA (gene) is added, which causes the DNA to flow into the plant cells. The plant cells then incorporate the new gene(s); and thus they have been genetically engineered.

The essence of the WHISKERS' technology is the small needle-like silicon carbide "whisker" (0.6 microns in diameter and 5-80 microns in length) which is used in the following manner. A container holding a "transformation cocktail" composed of DNA (e.g., agronomic gene plus a selectable marker gene), embryogenic corn tissue, and silicon carbide "whiskers" is mixed or shaken in a robust fashion on either a dental amalgam mixer or a paint shaker. The subsequent collisions between embryogenic corn cells and the sharp silicon carbide "whiskers" result in the creation of small holes in the plant cell wall through which DNA (the agronomic gene) is presumed to enter the cell. Those cells receiving and incorporating a new gene are then induced to grow and ultimately develop into fertile transgenic plants.

Not surprisingly, the fibrous, needle-like "whiskers" form of silicon carbide is a pulmonary health hazard and therefore must be handled much differently from non-fibrous silicon carbide powders that contain no whiskers. The two silicon carbide forms, powder and fibrous whiskers, are regulated much differently, with the British Columbian (Canadian) Occupational Health and Safety (OHS) regulating the fibrous form the same as asbestos at 0.1 fiber per cc (f/cc) exposure limit, whereas the ordinary, non-fibrous form has an exposure limit of 3-10 mg/cubic meter. Silicon carbide whiskers were shown to generate mutagenic reactive hydroxyl radicals in a manner similar to asbestos and to cause DNA strand breakage; silicon carbide powder did not cause such effects (Svensson et al., 1997).

Breaching the plant cell wall using silicon carbide powder does not direct any DNA associated with the powder to the plant nucleus, although this will happen at a low frequency. This problem can be overcome if the DNA is directed to the nucleus, as occurs in natural infections of *A. tumefaciens* or by certain viruses. Nuclear localization signal sequences (NLSs) guide the protein and any associated nucleic acid to the plant nucleus.

Genes successfully introduced into plants using recombinant DNA methodologies include, but are not limited to, those coding for the following traits: seed storage proteins, including modified 7S legume seed storage proteins (see, for example, U.S. Pat. Nos. 5,508,468, 5,559,223 and 5,576,203); herbicide tolerance or resistance (see, for example, De Greef et al., Bio/Technology 7:61 (1989); U.S. Pat. No. 4,940,835; U.S. Pat. No. 4,769,061; U.S. Pat. No. 4,975,374; Marshall et al. (1992) Theor. Appl. Genet. 83, 435; U.S. Pat. No. 5,489,520; U.S. Pat. No. 5,498,544; U.S. Pat. No. 5,554,798; Powell et al., Science 232:738-743 (1986); Kaniewski et al., Bio/Tech. 8:750-754 (1990)); Day et al., Proc. Natl. Acad. Sci. USA 88:6721-6725 (1991)); phytase (see, for example, U.S. Pat. No. 5,593,963); resistance to bacterial, fungal, nematode and insect pests, including resistance to the lepidoptera insects conferred by the Bt gene (see, for example, U.S. Pat. Nos. 5,597,945 and 5,597,946; Johnson et al., Proc. Natl. Acad. Sci. USA, 86:9871-9875 (1989); Perlak et al., Bio/Tech. 8:939-943 (1990)); lectins (U.S. Pat. No. 5,276,269); flower color (Meyer et al., Nature 330:677-678 (1987); Napoli et al., Plant Cell 2:279-289 (1990); van der Krol et al., Plant Cell 2:291-299 (1990)); Bt genes (Voisey et al., supra); neomycin phosphotransferase II (Quesbenberry et al., supra); the pea lectin gene (Diaz et al., Plant Physiology 109(4): 1167-1177 (1995); Eijsden et al., Plant Molecular Biology 29(3):431-439 (1995)); the auxin-responsive promoter GH3 (Larkin et al., Transgenic Research 5(5):325-335 (1996)); seed albumin gene from sunflowers (Khan et al., Transgenic Research 5(3):179-185 (1996)); and genes encoding the enzymes phosphinothricin acetyl transferase, beta-glucuronidase (GUS) coding for resistance to the Basta® herbicide, neomycin phosphotransferase, and an alpha-amylase inhibitor (Khan et al., supra), each of which is expressly incorporated herein by reference in their entirety.

For certain purposes, different antibiotic or herbicide selection markers may be preferred. Selection markers used routinely in transformation include the nptII gene which confers resistance to kanamycin and related antibiotics (see, for example, Messing & Vierra, Gene 19: 259-268 (1982); Bevan et al., Nature 304:184-187 (1983)), the bar gene which confers resistance to the herbicide phosphinothricin (White et al., Nucl Acids Res 18: 1062 (1990), Spencer et al., Theor Appl Genet. 79: 625-631 (1990)), and the dhfr gene, which confers resistance to methotrexate (Bourouis et al., EMBO J. 2(7): 1099-1104 (1983)).

A transgenic plant formed using *Agrobacterium, Rhizobium, Mesorhizobium* or *Sinorhizobium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Assuming normal hemizygosity, selfing will result in maximum genotypic segregation in the first selfed recombinant generation, also known as the R1 or $R_1$ generation. The R1 generation is produced by selfing the original recombinant line, also known as the R0 or $R_0$ generation. Because each insert acts as a dominant allele, in the absence of linkage and assuming only one hemizygous insert is required for tolerance expression, one insert would segregate 3:1, two inserts, 15:1, three inserts, 63:1, etc. Therefore, relatively few R1 plants need to be grown to find at least one resistance phenotype (U.S. Pat. Nos. 5,436,175 and 5,776,760).

As mentioned above, self-pollination of a hemizygous transgenic regenerated plant should produce progeny equivalent to an F2 in which approximately 25% should be homozygous transgenic plants. Self-pollination and testcrossing of the F2 progeny to non-transformed control plants can be used to identify homozygous transgenic plants and to maintain the line. If the progeny initially obtained for a regenerated plant were from cross-pollination, then identification of homozygous transgenic plants will require an additional generation of self-pollination (U.S. Pat. No. 5,545,545).

Breeding Methods

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative*

*Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, *In Hybridization of Crop Plants*.

It should be understood that the examples and embodiments described herein are for illustrative purposes only and that various modifications or changes in light thereof will be suggested to persons skilled in the art and are to be included within the spirit and purview of this application.

EXAMPLES

Example 1

Use of a Plant Pathogen to Isolate Bacteriophage Capable of Infecting a Gram Negative Plant Pathogen, *Xanthomonas pelargonii*

An overnight culture of *X. campestris* pv. *pelargonii* (syn. *X. pelargonii*) strain CHSC was grown at 30° C. in PYGM medium (peptone, yeast extract, glycerol and morpholinepropanesulfonic acid; DeFeyter et al. 1990) with moderate shaking. Five ml of this overnight culture plus 50 ml of unsterilized water taken from the edge of a large pond in an agricultural setting was added to 50 ml of PYGM plus 2.5 g $CaCO_3$ and allowed to incubate at 30° C. for 48 hours without shaking. Following incubation, 1 ml of this enrichment culture was centrifuged for 1 minute at 5000 g to remove most bacteria and debris, and 500 μl of the supernatant was removed and sterilized with a drop of chloroform. Droplets of this supernatant were placed atop an overlay plate containing strain CHSC in top agar. Overlay plates were PYGM agar plates overlayed with 200 μl of overnight CHSC broth culture added to 3 ml 0.7% water agar held at 50° C. and allowed to cool and solidify. Plaques were observed after 24 hrs. incubation; these were collected by scraping the plaques from the plates, titered and stored according to standard procedures (Sambrook et al., 1989). These mixtures of phage were then purified from single plaques, and individual phage tested for bacterial host range against *X. citri* strain B21.2, *X. campestris* strain 528, and *Ralstoma solanacearum* strain G2. All phage were specifically able to attack only *X. pelargonii* strain CHSC and did not infect the other strains.

Example 2

Use of Agar Plate Overlay Assays to Characterize Phage Host Range and to Identify Phage with an Ability to Kill Bacterial Hosts that they Cannot Infect PYGM plates were overlaid with *X. pelargonii* CHSC and droplets of various purified phage samples obtained from Example 1 were added to the plates and incubated at 30° C. for 48 hours. All phage were able to infect CHSC and cause clear zones of lysis. Cell suspensions of overnight broth cultures of *X. citri* B21.2, *X. campestris* 528 and *R. solanacearum* G2 were added to 0.7% water agar as described in Example 1 and individually overlayed on the phage infected CHSC plates.

Plates were incubated an additional 48 hrs at 30° C. and phage were evaluated for ability to kill Gram negative bacteria that they could not infect from the outside. Some phage exhibited presence of a strong, apparently diffusible killing factor for all bacteria tested. Phage isolate 15 (P15) was selected for sequencing and further evaluation.

Example 3

Use of Genomic Sequencing and Annotation Techniques to Identify Gene Candidates from Phage P15 Encoding Proteins with Ability to Kill Bacteria from the Outside The P15 genome was completely sequenced in order to identify the gene(s) expressing the diffusible killing factor. P15 DNA was made according to standard protocols using *X. pelargonii* strain CHSC as the host bacterium. The P15 DNA was digested with EcoRV, yielding eleven fragments, ranging in size from 12.4 kb to 357 bp. Most of the fragments were cloned; some were not cloned, despite repeated attempts, most likely due to the presence of restriction endonucleases and holins. The cloned DNA fragments were used directly for sequencing, using vector-based primers initially, and primer walking thereafter until each fragment was completed. Fragments that were not cloned were sequenced using P15 genomic DNA. Fragment assembly was accomplished using P15 genomic DNA and primers extending outside each fragment in both directions. P15 has a double stranded DNA genome which is 55,770 bp in length (GenBank NC__007024). The sequence of P15 is also provided as SEQ ID No. 1 in priority document PCT/US2004/015099, wherein both the sequence per se and PCT/US2004/015099 are incorporated in their entireties herein for all purposes.

ORF analysis of the sequenced phage was done using a combination of several programs including PromScan, Terminator (GCG), GeSTer (Unniraman et al. 2001, 2002), Glimmer, Genie, Codon preference (GCG), ORF finder (NCBI) and Blast (NCBI) analyses. Potential Shine-Delgarno sequences were identified manually by examining the sequence. Using default Glimmer settings, only 32 ORFs were identified; none of these ORFs corresponded to functional genes later identified as holins or BOMB by functional analyses, although lysY, predicted to encode an endolysin, was identified. After identifying the promoters and terminators in the genome, manual analysis of all ORFs using Codon preference (GCG) allowed the identification of an additional 52 ORFs, including those predicted to encode holins. The genome encoded 84 putative ORFS (GenBank NC__007024). There were several predicted ORFs of unknown function. Phage P15 ORF "BC" (bombBC; SEQ ID No. 1) was predicted to encode a 17.9 kD protein with a charge of −0.5 at neutral pH (BombBC; SEQ ID No. 2). SEQ ID No. 2 of the present continuation-in-part application is the same as SEQ ID No. 82 in U.S. application Ser. No. 10/556,563 and PCT/US2004/015099. The present application claims priority to each of these applications and both applications are incorporated in their entireties (i.e., including but not limited to their sequence listings) herein for all purposes. This ORF was among several Phage P15ORFs cloned, expressed and functionally evaluated for evidence of effect on the *E. coli* outer membrane.

Example 4

Use of a Phytoalexin and Inducible Gene Expression Systems to Identify Candidate Genes Encoding Proteins With Ability to Kill from the Outside As detailed above, bacteriophage are known to encode proteins that are able to degrade the bacterial cell wall (endolysins) and proteins that are able to degrade or breach the bacterial inner membrane (holins). Unknown until now are bacteriophage proteins with ability to degrade or breach the bacterial outer membrane (ie., "BOMB" proteins), nor are any assays described to identify such proteins. The predicted peptide coding regions of the P15 putative holin, holZ (SEQ ID No. 27 in U.S. application Ser. No. 10/556,563 and PCT/US2004/015099) its endolysin, lysY(SEQ ID No. 26 in U.S. application Ser. No. 10/556,563 and PCT/US2004/015099), and its BOMB, bombBC(SEQ ID No. 82 in U.S. application Ser. No. 10/556,563 and PCT/US2004/015099) were amplified by polymerase chain reaction (PCR) from the P15 phage DNA and cloned in pGemT without promoters. These coding regions were operably fused with a repressible promoter in a modified pET27b expression vector system using *E. coli* strain BL21 DE3 (Novagen). In the case of bombBC, two versions were created, one of them with, and the other without, a pelB leader sequence. This leader sequence assured export of bombBCacross the inner membrane to the bacterial periplasm. Experiments were conducted to compare the effect of expression of these three genes in pET27b by comparison with the empty vector in liquid cultures. In addition, experiments were conducted to compare the effect of expression of the holin, holZwith the BOMB, bombBC, in BL21 DE3 cells that also constitutively expressed an endolysin gene, lysS. Cells were cultured on agar plates under glucose repression, and then grown in liquid culture medium without repression. Cells were then induced by addition of 1 mM IPTG and the optical density (OD) of the cultures at 600 nm were compared at different times after induction. Results are presented in Table 1 below.

Induced expression of the holin, HolZ, without the endolysin LysS, caused quasilysis; the optical density of the culture increased somewhat and then declined to the starting density. There was no evidence of cell debris in these cultures. By contrast, induced expression of HolZ with LysS caused immediate lysis, with obvious cell debris in the cleared lysate. These effects are characteristic of holins, which kill the cell by disrupting the inner membrane, but which cannot degrade the bacterial cell wall, and so cellular contents remain contained and there is no appearance of a lysate in the culture.

Induced expression of the endolysin, LysY, caused a slow reduction in cell density (not shown), and by contrast with the effects of HolZ expressed alone, cell lysis debris was apparent in these cultures. Since LysY was cloned without a leader sequence, this endolysin appeared to behave similarly to lysozyme, and exhibited some ability to penetrate or permeabilize the bacterial inner membrane, allowing it to reach and degrade the bacterial cell wall, causing lysis.

Induced expression of the BOMB protein BombBC caused quasilysis that looked similar to that caused by HolZ; the optical density of the culture increased somewhat and then declined to the starting density. There was also no evidence of cell debris in these cultures. However, and by contrast with HolZ combined with LysS, BombBC combined with LysS did not cause lysis, but rather BombBC combined with LysS appeared to have no lytic effect, indicating that the inner bacterial membrane was intact and LysS could not reach the periplasm and attack the cell wall. This strongly suggested that the activity of BombBC was qualitatively different from that of a holin, which breaches the inner membrane, or an endolysin, which degrades the murein or peptidoglycan cell wall.

In addition, berberine chloride, a commercially prepared, plant derived, antimicrobial compound (a "phytoalexin") worked synergistically with BombBC to reduce culture density. This synergistic effect was not seen with either a holin nor an endolysin. Berberine may be used to assay for defects in the LPS barrier and/or efflux pumping ability of phytopathogenic bacteria (Reddy et al., 2007). Bacteria are sensitive to berberine in a concentration dependent manner. Any berberine that leaks through the LPS must be actively pumped out (effluxed) for bacterial survival; if either the LPS is breached or the efflux pumps are disabled, bacteria are unable to grow in the presence of berberine. When berberine (5,6-dihydro-9,10-dimethoxybenzo-1,3-benzodioxoloquino-lizimium, an alkaloid DNA intercalating agent; Schmeller et al., 1997), was added (5 micrograms/ml) to cells carrying bombBC and grown in liquid culture in these experiments, cell death was much more rapid when BombBC was expressed. Addition of berberine at the same concentration to BL21 DE3 cells carrying the pET vector alone had little effect. The synergistic effect of berberine with expressed BombBC demonstrated that BombBC acted on the outer membrane, or LPS protective layer, of the bacterial cells and suggested that berberine and other agents that must be actively effluxed from bacterial cells may be used as part of an additional gene expression assay to distinguish Bomb genes from other bacteriophage genes that kill bacterial cells upon expression (eg., endolysin and holin genes).

TABLE 1

Effect of expression of holin HolZ, endolysin LysY and BOMB BombBC genes cloned from phage P15 on growth of *E. coli* BL21 DE3 cells in liquid culture in the presence or absence of the phytoalexin berberine.

| | | 0 hr PI | 3 hr PI | 18 hr PI | 24 hr PI |
|---|---|---|---|---|---|
| BL21DE3/ pET vector only | Uninduced | 0.5 | 1.0 | 0.9 | 0.9 |
| | Induced | 0.5 | 0.9 | 0.8 | 0.8 |
| | Induced + berberine | 0.5 | 0.9 | 0.7 | 0.7 |
| BL21DE3/ P15 holZ (holin) | Uninduced | 0.6 | 1.0 | 1.0 | 1.0 |
| | Induced | 0.6 | 0.8 | .6 | .6 |
| | Induced + berberine | ND | ND | ND | ND |
| BL21DE3/ plysS/holZ (holin + endolysin) | Uninduced | 0.4 | 0.7 | ND | ND |
| | Induced | 0.4 | 0.1 | ND | ND |
| | Induced + berberine | ND | ND | ND | ND |
| BL21DE3/ bombBC (BOMB) | Uninduced | 0.5 | 1.0 | 0.8 | 0.8 |
| | Induced | 0.5 | 0.8 | 0.7 | 0.6 |
| | Induced + berberine | 0.5 | 0.6 | 0.5 | 0.4 |
| BL21DE3/ plysS/ bombBC (BOMB + endolysin) | Uninduced | 0.34 | 1.1 | 1.2 | 1.4 |
| | Induced | 0.34 | 0.8 | 0.35 | 0.4 |
| | Induced + berberine | ND | ND | ND | ND |

PI, Post-Inoculation;
ND, Not Determined.

Example 5

Use of P3rpoH::lacZ Reporter to Confirm Effect of BOMB Protein on Bacterial LPS

*E. coli* strains ADA410 carries a P3rpoH::lacZ reporter gene that is selectively activated when the LPS or outer membrane of the cells are damaged (Shapiro and Baneyx, 2002). The bombBC coding region was recloned into the pMAL expression vector (New England Biolabs, Ipswich, Mass.), overexpressed in *E. coli* BL21 DE3 cells, and purified (FIG. 1). Ten microliter droplets of the purified protein preparation were dropped onto a fresh suspension of ADA410 cells plated on LB agar containing 5-bromo-4-chloro-3-indolyl Beta-D-galactopyranoside (X-gal), along with resuspension buffer as a control. Blue color slowly developed and intensified over a 24 hr period of growth around the ADA410 cells, confirming a detrimental effect of BombBC on the bacterial LPS.

Example 6

Construction of Bombbc Expression Cassettes in Plant Expression Vectors

The CaMV promoter from pB1221 (Clontech, Palo Alto, Calif.) was enzymatically recloned into the polylinker cloning site of pCAMBIA0390 (Cambia, Can berra, AU), which has a left T-DNA border, the polylinker site, a NOS transcriptional terminator and right T-DNA borders, creating pIPG700. The phage P15 bombBC gene was enzymatically recloned into pIPG700 downstream from the CaMV promoter and upstream from the NOS terminator, creating pIPG780. A 24 amino acid plant signal peptide derived from a protein known to accumulate in the citrus xylem, P12 (GenBank Accession #AF015782; Ceccardi et al., 1998) was used to create a xylem secretion signal leader (SEQ ID No. 3 and SEQ ID No. 4). The xylem secretion signal peptide sequence was amplified from *Citrus sinensis* (sweet orange) by PCR and cloned upstream of the bombBC gene and resulting in a translational gene fusion between P12 and BombBC (SEQ ID No. 5) on pIPG780. Clone pIPG780 was subsequently used for transient expression assays in the dicots: pepper, citrus and geranium.

The P12::BombBC gene (SEQ ID No. 5) was enzymatically recloned from pIPG780 into pCAMBIA1305.2 (Cambia, Can berra, AU), such that the gene was driven from the reverse CaMV promoter of pCAMBIA1305.2, forming pIPG787. pCAMBIA1305.2 carries the hygromycin resistance gene driven by a dual CaMV promoter for plant selection. The P12::BombBC (SEQ ID No. 5) gene was also enzymatically recloned from pIPG780 into pCAMBIA2301 (Cambia, Can berra, AU), such that the BombBC gene was driven from the reverse CaMV promoter of pCAMBIA2301, forming pIPG786.

pCAMBIA2301 carries the kanamycin resistance gene driven by a dual CaMV promoter for plant selection. pIPG786 was used for transformation and regeneration of tobacco and citrus, while pIPG787 was used for transformation of geranium and rice.

Example 7

Use of Transient Expression of BombBC in Sweet Pepper Plants to Demonstrate Enhanced Resistance to *Xanthomonas* and *Ralstoma*

For transient expression assays, the plant transformation and expression vector pIPG780 was moved into *A. tumefaciens* strain GV2260 by either electroporation or bacterial conjugation as described (Kapila et al., 1997). GV2260 carrying pIPG780 was used for transient expression in pepper and geranium plants as described (Kapila et al. 1997; Duan et al., 1999; Wroblewski et al. 2005). Cultures of *Agrobacterium* harboring the constructs of interest were grown in minimal medium in the presence of acetosyringone to induce the *Agrobacterium vir* genes. The optical density of the cultures was maintained at 0.008 for pepper and at 0.25 for geranium. Strain GV2260 carrying pIPG780 or empty vector control was first flooded into the apoplastic spaces of sweet pepper (*Capsicum*) leaves through open stomata by injection using a tuberculin syringe without a needle. An area of from 2 to 10

$cm^2$ of leaf was flooded and the area inoculated was then circled with a permanent marker. This was followed 3 days later by challenge inoculations within the previously inoculated area, again by syringe injection, this time with ca. $2\times10^6$ colony forming units (cfu) of either *X. pelargomi* strain CHSC or *R. solanacearum*, both grown overnight in liquid cultures. This gave an inoculum density of each pathogen of about $2\times10^4$ cfu/$cm^2$. Both strains used were published reference strains, confirmed pathogenic on their hosts: *X. pelargonii* attacks only geranium and causes bacterial blight disease of geranium, while *R. solanacearum* attacks primarily plants in the Solanaceae family (potato and tomato). Sweet pepper is a nonhost of both pathogens. (Plants that are attacked in nature are considered to be "hosts" of the indicated pathogens. All other plants are considered to be "nonhosts" of the indicated pathogens. When these same pathogens are inoculated at the indicated densities onto nonhost plants or onto host plants carrying certain resistance (R) genes, a rapid hypersensitive response (HR), is observed. The HR appears as a confluent, necrotic, collapsed zone at the inoculation site within 24-48 hrs.).

Results were assessed visually according to presence or absence of HR symptoms observed after 48 hrs. In all cases, a "split leaf" assay was used in which pIPG780 was inoculated on one half of the leaf and the empty vector control was inoculated on the other half of the same leaf. In repeated experiments; HR symptoms elicited on the control side of the inoculated leaf by either *X. pelargonii* or *R. solanacearum* were abolished in the presence of transiently expressed BombBC on pIPG780.

Due to the effects of BombBC in compromising the LPS barrier of *E. coli* to allow the phytoalexin berberine to penetrate and kill the bacterium in Example 4 and the indirect evidence of damaging the LPS barrier of *E. coli* in Example 5, we deduce that the native phytoalexins of pepper plants, in combination with the BombBC transiently expressed in pepper plants, killed or inhibited growth of both *Xanthomonas* and *Ralstoma*, thereby preventing the HR in these experiments.

Example 8

Use of Transient Expression of BombBC in Geranium (*Pelargonium×hortorum*) Plants to Demonstrate Enhanced Resistance to *Ralstoma*

In order to determine if *Ralstoma* pathogens were also affected by BombBC expressed in host plants, as opposed to nonhost plants such as pepper, assays similar to those described in Example 7 above were performed, this time using Florists' geranium (Pelargonium×hortorum). This was done in order to confirm that the killing or disabling of this pathogen's ability to elicit an HR on nonhosts also extended to pathogens of susceptible host plants. Assays identical to those described in Example 7 were performed using florist's geranium plants, except that for these pathogenicity assays in a plant that is highly susceptible to disease from this pathogen, the results were examined daily for a period of from 2 to 7 days after challenge inoculation. Again, the results were similar to those described for the HR in Example 7. Pathogenic symptoms caused by *X. pelargonii* were greatly reduced when pIPG780 was used. In addition, cell counts taken from these regions demonstrated a 100× drop in the number of colony forming units in plant leaves expressing BombBC vs. control leaves. These results confirmed and extended the concept that BombBC can be expressed in plants for the purpose of killing or disabling Gram-negative pathogenic bacteria to include host plants, most likely due to the combined effects of native phytoalexins produced by the host plant and transient expression of BombBC to disable the LPS barrier of the pathogen.

Example 9

Use of Transient Expression of BombBC in Citrus Plants to Demonstrate Enhanced Resistance to *Xanthomonas citri*

In order to determine if *Xanthomonas* pathogens were also affected by BombBC expressed in host plants, as opposed to nonhost plants such as pepper, assays similar to those described in Examples 7 and 8 above were performed, this time using grapefruit (*Citrus paradisi*) plants inoculated with *X. citri*, causal agent of citrus canker disease. This agent is a regulated pathogen, and such inoculations had to be performed under strict quarantine.

These experiments were done in order to confirm that the degradation or breaching of the LPS of *Xanthomonas* and subsequent killing of the pathogen, affecting its ability to elicit an HR on nonhosts also extended to pathogens of susceptible host plants. Assays identical to those described in Examples 7 and 8 were performed using citrus, except that for these pathogenicity assays in a plant that is highly susceptible to disease from this pathogen, the results were examined daily for a period of from 6 to 14 days after challenge inoculation. Again, the results were similar to those described for the HR in Example 7 or the pathogenic reaction in Example 8. Pathogenic symptoms caused by *X. citri* were greatly reduced when pIPG780 was used. These results confirmed and extended the concept that BombBC can be expressed in plants for the purpose of killing or disabling Gram-negative pathogenic bacteria to include host plants, most likely due to the combined effects of native phytoalexins produced by the host plant and transient expression of BombBC to disable the LPS barrier of the pathogen.

Example 10

Creation of Transgenic Geranium (*Pelargonium×hortorum*) Using bombBC

Figure 2:
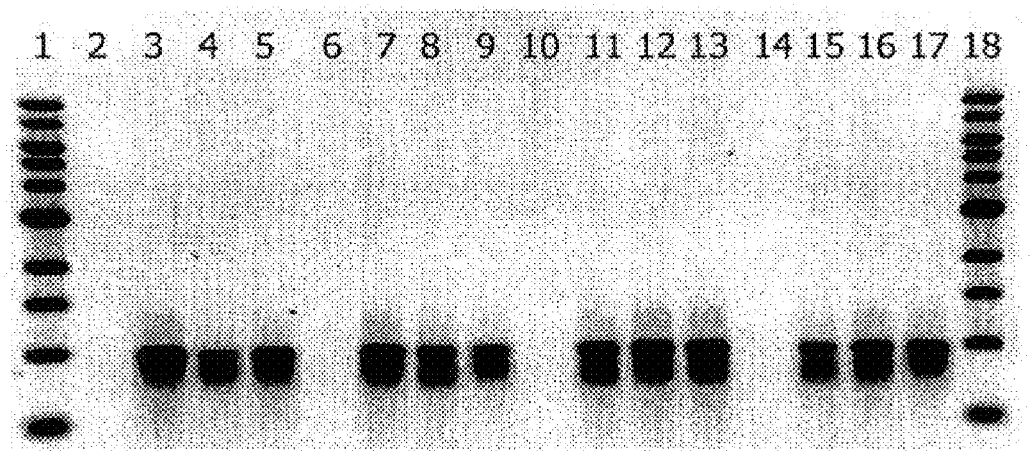
FIG. 2 shows PCR confirmation of transformation of four plant species using bombBC, including 3 plants each of Florist's geranium (*Pelargonium×hortorum*) cv. Avenida (Lanes 3, 4, 5), citrus (*Citrus sinensis×Poncirus trifoliata*) cv. Carizzo, tobacco (*Nicotiana tobacum*) cv. *Xanthi*, and rice (*Oryza sativa* japonica) cv. TP309. Lane 1, 1 kb DNA ladder; 2, nontransgenic Avenida control; 3, Av250; 4, Av386; 5, Av387; 6, nontransgenic Carizzo control; 7, C12; 8, C17; 9, C18; 10, nontransgenic *Xanthi* control; 11, X473; 12, X480; 13, X901; 14, nontransgenic TP309 control, 15, TP147; 16, TP170; 17, TP192; 18, 1 kb DNA ladder. PCR primers used were IPG872 (5'-tca gcc act cga tgc cgt c) and IPG911 (5'-gca cga ttc aag agt agg). The expected PCR product in all cases is 974 bp.

Transgenic geranium (*Pelargonium×hortorum*) cv. Avenida were created using *Agrobacterium tumefaciens* and *Rhizobium* spp. using bombBC gene cloned into pIPG787. The most efficient methods for production of transgenic geraniums were achieved using either *A. tumefaciens* (Robichon et al., 1995. Approximately 9% PCR positive geranium petiole explants were confirmed (of the 360 total petioles subjected to the transformation protocols. A total of 33 transgenic geranium were obtained, based on PCR amplification of the bombBC gene (FIG. 2). Selected plants were asexually reproduced and challenge inoculated with different pathogens as described below. These results demonstrated that the bombBC gene, shown to be expressed in transient expression assays, could be stably transformed and presumably expressed in geraniums at efficiencies equivalent to those obtained using empty vector or another gene construct, indicating that BombBC was not detrimental to geranium plants.

Example 11

Creation of Transgenic Tobacco (*Nicotiana tabaccum*) Using bombBC

Transgenic *Nicotiana tabaccum* cv. *Xanthi* plants were created using *Agrobacterium tumefaciens* and *Rhizobium* spp. using the bombBC gene cloned into pIPG786. The most efficient methods for production of transgenic tobacco were achieved using the leaf disc method with *A. tumefaciens* as described (Horsch et al. 1985). Transformants were selected on MS media (Murashige and Skoog 1962) containing kanamycin at 100 μg/ml. Approximately 21% PCR positive tobacco explants were confirmed (of the 235 total leaf discs subjected to the transformation protocols. A total of 50 transgenic tobacco plants were obtained, based on PCR amplification of the bombBC gene FIG. 2). Selected plants were both sexually and asexually reproduced and challenge inoculated with different pathogens as described below. These results demonstrated that the bombBC gene, shown to be expressed in transient expression assays, could be stably transformed and presumably expressed in tobacco at efficiencies equivalent to those obtained using empty vector or another gene construct, indicating that BombBC expression was not detrimental to tobacco plants.

Example 12

Creation of Transgenic Citrus (*Citrus sinensis*×*Poncirus trifoliata*) Using bombBC Transgenic citrus (*Citrus sinensis*×*Poncirus trifoliata*) cv. Carizzo plants were created using *Agrobacterium tumefaciens* and *Rhizobium* spp. using bombBC gene cloned into pIPG786. The most efficient methods for production of transgenic citrus were achieved using *A. tumefaciens* applied to etiolated citrus stem sections as described (Moore et al., 1992). Approximately 6% PCR positive citrus stem explants were confirmed (of the 650 total stem sections subjected to the transformation protocols. A total of 40 transgenic citrus plants were obtained, based on PCR amplification of the bombBC gene (FIG. 2). Selected plants were asexually reproduced and challenge inoculated with different pathogens as described below. These results demonstrated that the bombBC gene, shown to be expressed in transient expression assays, could be stably transformed and presumably expressed in citrus at efficiencies equivalent to those obtained using empty vector or another gene construct, indicating that BombBC was not detrimental to citrus plants.

Example 13

Creation of Transgenic Rice (*Oryza sativa* Japonica) Using bombBC

Transgenic rice (*Oryza sativa* japonica) cv. TP309 were created using *Agrobacterium tumefaciens* and *Rifizobium* spp. using bombBC gene cloned into pIPG787. The most efficient methods for production of transgenic rice were achieved using *A. tumefaciens* applied to rice callus produced from seed as described (Hiei et al., 1997). Approximately 20% PCR positive rice explants were confirmed (of the 305 total number of calli subjected to the transformation protocol. A total of 60 transgenic rice plants were obtained, based on PCR amplification of the bombBC gene. Selected plants were sexually reproduced and challenge inoculated with different pathogens as described below. These results demonstrated that the bombBC gene, shown to be expressed in transient expression assays, could be stably transformed and presumably expressed in rice at efficiencies equivalent to those obtained using empty vector or another gene construct, indicating that BombBC was not detrimental to rice plants.

Example 14

Use of Asexually Reproduced Progeny of Transgenic Geranium, Citrus and Tobacco Plants to Obtain Cloned bombBC Plants Transgenic geranium, citrus and tobacco plants were obtained as set forth in Examples 10, 11 and 12. The transgenic geranium, citrus and tobacco plants were asexually propagated to produce progeny clones using techniques well known to one skilled in the art of geranium, citrus or tobacco propagation. For geranium, tobacco and other vegetative species that are normally propagated by taking cuttings, an internode with two nodes are cut from a mother plant and rooted, normally using a support medium, with or without root inducing hormones, producing a single new plant for each such clone or "cutting". The cuttings were in all cases genetically identical to the mother plant (ie., 100% PCR positive for BombBC). For citrus and similarly propagated woody species, a "scion" cutting is taken from a transgenic stem section with leaves and grafted or spliced onto a nontransgenic rootstock, such that the roots and lower main stem are comprised of the nontransgenic rootstock, while the upper main stem and shoots are comprised of the transgenic scion. The scion cuttings were in all cases genetically identical to the mother plant (ie., 100% PCR positive for BombBC); the genetic modifications performed in the mother plant were stable. These results demonstrated that the genetic modifications performed in the mother plant were stable through at least one asexual generation.

Example 15

Use of Sexually Reproduced Progeny of Transgenic Rice and Tobacco Plants to Obtain Cloned bombBC Plants Transgenic diploid rice and tobacco plants were obtained as set forth in Examples 11 and 13. The transgenic ($T_0$ generation) rice and tobacco plants were self-pollinated and the seed ($T_1$ generation) was harvested from the self-pollinated plants, processed, planted, and progeny plants grown from the self-pollinated-seed. PCR assays were used to determine that the $T_1$ progeny plants all had a classical genetic 3:1 ratio, wherein ¾ of the plants (¼ homozygous transgenic and ½ heterozygous transgenic plants) were found to be transgenic by PCR tests, and ¼ of the plants were nontransgenic. These tests showed that that the introduced nucleic acid molecules encoding bombBC were stably integrated into both rice and tobacco using the methods of the present invention and that bombBC was also heritable.

Example 16

Use of bombBC Expressed in Transgenic Geranium (*Pelargonium*×*hortorum*) Host Plants to Confer Resistance to *Xanthomonas pelargonii* and *Ralstonia solanacearum*

Pathogen challenge inoculations of transgenic Florist's geranium (*Pelargonium*×*hortorum*) plants expressing active BombBC and of asexually propagated Florist's geranium plants expressing active BombBC were conducted using *X. pelargonii* and *R. solanacearum*. The transgenic parental or asexually produced progeny clones obtained from the transgenic parental plants reduced disease symptoms.

Figure 3:
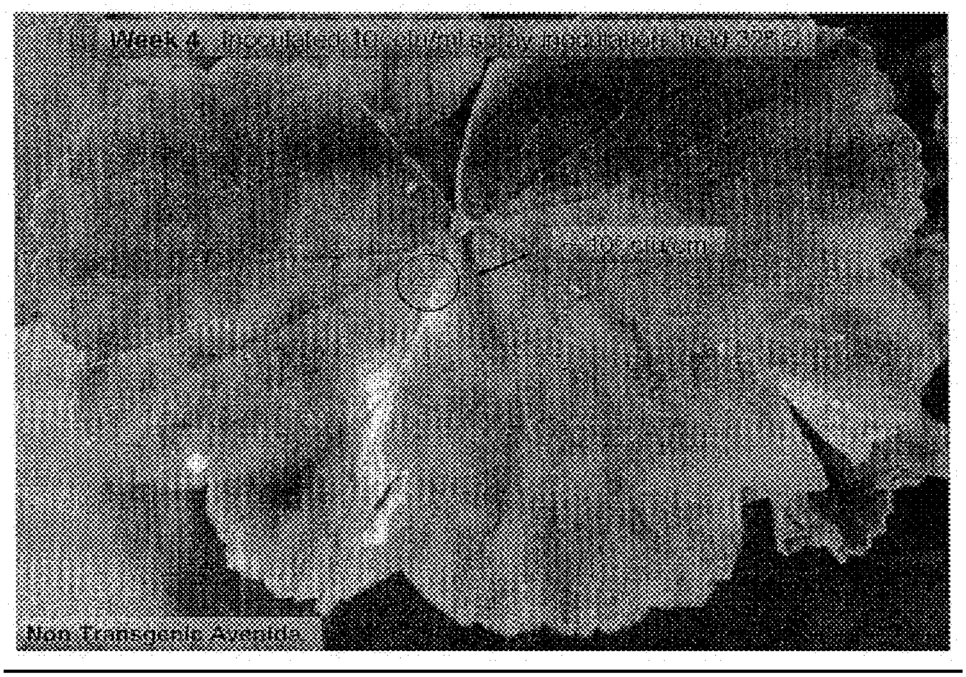
FIG. 3 shows typical symptoms of bacterial blight on a nontransgenic Florist's geranium (*Peargonium×hortorum*) cultivar "Avenida" leaf inoculated with *X. pelargonii* cells sprayed on the leaves at a concentration of $10^7$ colony forming units per milliliter (cfu/ml) and also inoculated using scissors dipped in $10^9$ cfu/ml of *X. pelargonii* cells to clip the leaves in several places. Following inoculation, plants were held at 32° C. The circled region was cut out, and contained ca. $10^5$ cfu/$cm^2$ live *X. pelargonii* cells (for details, refer Example 11 below). Photo taken four weeks after inoculation.

Inoculations were performed using liquid culture grown *X. pelargonii* cells, sprayed on the leaves at a concentration of $10^7$ colony forming units per milliliter (cfu/ml) each. *X. pelargonii* was also inoculated using scissors dipped in $10^9$ cfu/ml of cells to clip the leaves in several places on the same plants that were sprayed. Following *X. pelargonii* inoculation, plants were held at 32° C. to encourage pathogen growth and symptom development. Four weeks after inoculation, photographs were taken of both nontransgenic geranium variety "Avenida" inoculated with *X. pelargonii* (FIG. 1) and transgenic geranium of the same variety "Avenida" expressing BombBC inoculated with *X. pelargonii* (FIG. 2), and circular sections totaling 1 square centimeter ($cm^2$) were removed using a cork borer from three inoculated leaves in the area most likely to contain pathogen cells (refer FIGS. 1 and 2). Consistently, $10^5$ cfu/ml of *X. pelargonii* was recovered from nontransgenic geranium variety "Avenida" plants at four weeks after inoculation (FIG. 3), and symptoms progressed systemically until the entire plant was dead, usually by 12 weeks after inoculation. However, no living *X. pelargonii* cells were recovered from transgenic geranium variety "Avenida" plants after five days following inoculation (FIG. 3), and there was no evidence of symptoms of geranium blight caused by *X. pelargonii*. These plants were immune to *X. pelargonii* infection.

Figure 4:
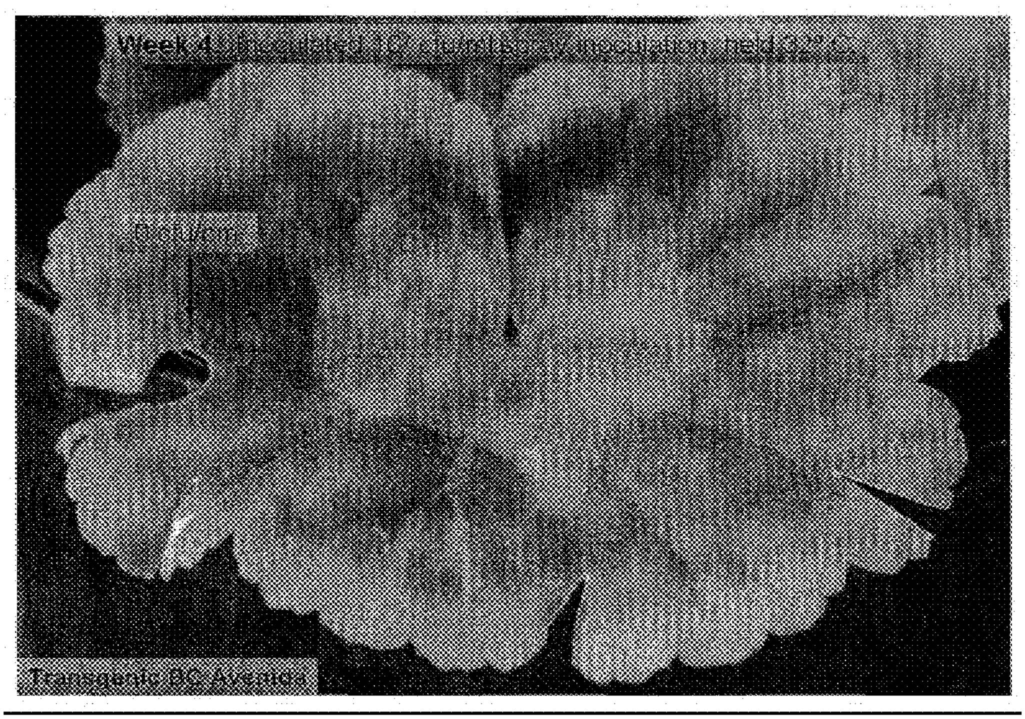
FIG. 4 shows a transgenic Florist's geranium (*Pelargonium×hortorum*) cultivar "Avenida" leaf expressing BombBC and inoculated at the same time and in the same manner as that described in the legend of FIG. 1. Following inoculation, plants were held at 32° C. The circular cut out region contained no detected *X. pelargonii* cells. Photo taken four weeks after inoculation.
Figure 5:
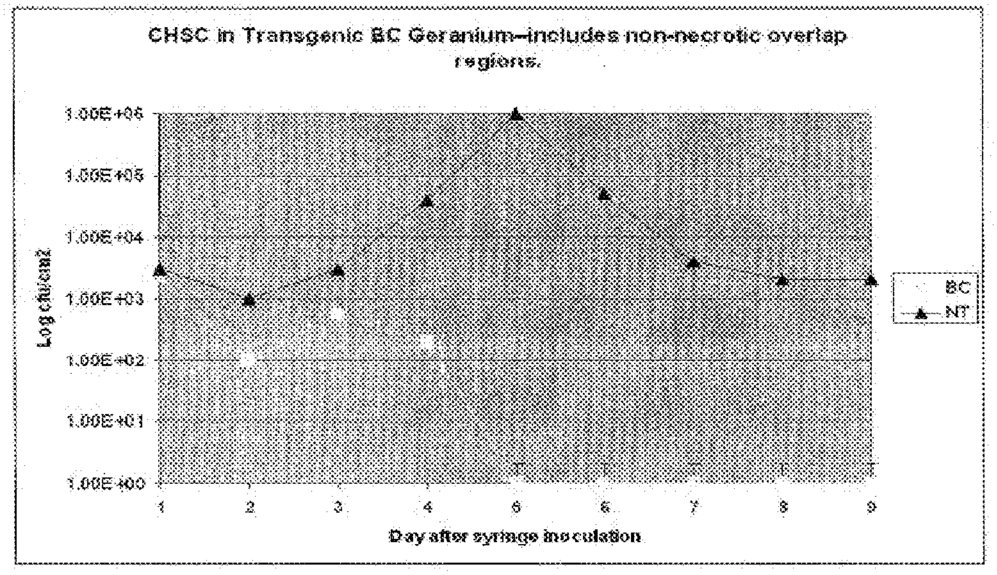
FIG. 5 shows growth of *X. pelargonii* strain CHSC inoculated on nontransgenic geranium (*Pelargonium×hortorum*) variety "Avenida" and rapid death of strain CHSC inoculated on transgenic variety "Avenida" expressing BombBC. Cell counts were taken daily for nine days by removing circular sections totaling 1 square centimeter ($cm^2$) using a cork borer from three inoculated leaves in the area most likely to contain pathogen cells (refer FIGS. 1 and 2). These leaf sections were macerated with a mortar and pestle and 1 milliliter of buffer, diluted using a 1:10 dilution series and 10 microliter drops placed on solid growth medium for counting. Consistently, a maximum cell density of $10^6$ cfu/ml of *X. pelargonii* was achieved in nontransgenic geranium variety "Avenida" plants after five days, and symptoms progressed steadily and systemically until the entire plant was dead, usually by 12 weeks after inoculation. However, no living *X. pelargonii* cells were recovered from transgenic geranium variety "Avenida" plants after five days following inoculation (FIG. 3), and there was no evidence of symptoms of geranium blight caused by *X. pelargonii*. These plants were both immune to *X. pelargonii* infection, and rapidly brought the artificially inoculated pathogen population to extinction.
Figure 6:
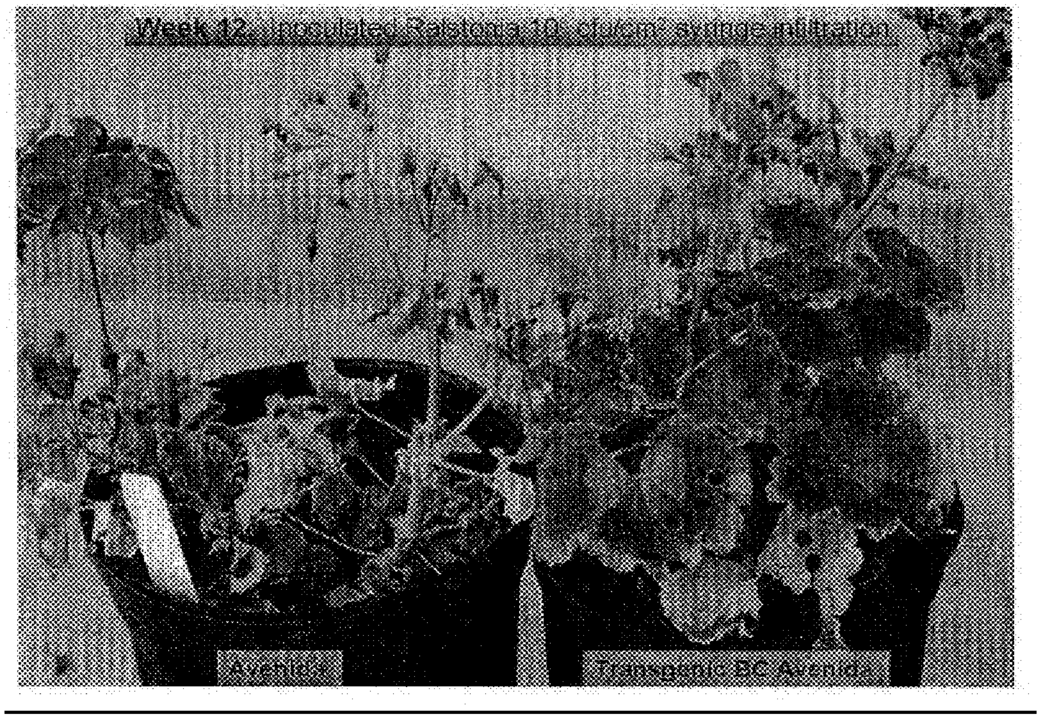
FIG. 6 shows a comparison of nontransgenic Florist's geranium (*Pelargonium×hortorum*) cultivar "Avenida" leaf inoculated with *R. solanacearum* cells inoculated by syringe infiltration of $10^6$ cfu/ml directly into the spongy mesophyl of leaves using the blunt end of a tuberculin syringe. In addition, these same syringe inoculated plants were also inoculated by adding 5 ml of a $10^7$ cfu/ml liquid culture directly to the soil of the potted plants geranium plants. Following inoculation, plants were held at 32° C. to encourage pathogen growth and symptom development. Four weeks after inoculation, photographs were taken of both nontransgenic geranium variety "Avenida" (left) and transgenic geranium of the same variety "Avenida" expressing BombBC (right). Typical symptoms of bacterial wilt developed on the nontransgenic plants, which died after 12 weeks. No symptom development, other than that which initially developed in, and stayed restricted to, the region of inoculation was observed on the transgenic variety "Avenida" expression BombBC (right).

In separate experiments, *R. solanacearum* strain Rsp673, originally isolated from geranium and known to be strongly pathogenic to geranium, was inoculated by syringe infiltration of $10^6$ cfu/ml directly into the spongy mesophyl of leaves using the blunt end of a tuberculin syringe. In addition, these same syringe inoculated plants were also inoculated by adding 5 ml of a liquid culture containing $10^7$ cfu/ml of cells directly to the soil of the potted geranium plants (refer FIG. 4). Following inoculation, plants were held at 32° C. to encourage pathogen growth and symptom development. Symptoms on transgenic BombBC geranium variety "Avenida" plants inoculated with *R. solanacearum*, causal agent of bacterial wilt, failed to progress past the leaf area where the pathogen was directly infiltrated and the disease never became systemic. In addition to suppressing disease, BombBC expression evidently killed the pathogen, since there were no detected *R. solanacearum* cells twelve weeks after inoculation of *R. solanacearum* on transgenic BombBC "Avenida" plants. By contrast, symptoms on nontransgenic "Avenida" plants progressed normally and systemically; by twelve weeks after inoculation of *R. solanacearum*, all nontransgenic "Avenida" plants had died from wilt disease caused by this pathogen (FIG. 4).

These tests confirm that the introduced nucleic acid molecules coding for the BombBC protein have been stably integrated into geranium using the methods of the present invention, and demonstrate that transgenic geraniums, whether vegetatively propagated or not, are resistant or immune from disease caused by *X. pelargonii* and *R. solanacearum*.

These results further demonstrate that transgenic geraniums, whether vegetatively propagated or not, kill *X. pelargonii* and *R. solanacearum* cells. These results also confirm and extend the demonstration of disruption of the LPS of Gram negative bacteria generally, as anticipated from tests of cells grown in culture and that such LPS disruption results in resistance to disease as anticipated from transient expression assays.

Example 17

Use of bombBC Expressed in Transgenic Tobacco Host Plants to Confer Resistance to *Ralstonia solanacearum*

Pathogen challenge inoculations of transgenic tobacco (*Nicotiana tabaccum* cv. *Xanthi*) plants expressing BombBC were conducted using *R. solanacearum*. Both sexually propagated (seeded, T1 generation from Example 15; Exp 3 in Table below) and asexually propagated (cuttings, T0 generation from Example 11; Exp. 1 and 2 in Table below)) tobacco plants were inoculated and compared, since the method of asexual propagation provides a healed over, but still significantly enlarged cut surface beneath the soil line that might facilitate entry by the soil-born pathogen.

*R. solanacearum* strain Rsp446, strongly pathogenic to tobacco, was In inoculated by adding 5 ml of a liquid culture containing $5\times10^7$ to $2\times10^8$ cfu/ml of cells directly to the soil of the potted tobacco plants. Following inoculation, plants were held at 32° C. to encourage pathogen growth and symptom development. Plants were examined daily and wilted plants exhibiting black vein symptoms were noted and discarded. The results, recorded as number of survivors/total tested, after 68 days were as follows:

| | Inoculum level | Control Cutting | Control Seeded | BombBC Cutting | BombBC Seeded |
|---|---|---|---|---|---|
| Exp. 1 | $5 \times 10^7$ | 7/19 (37%) | | 10/15 (63%) | |
| Exp. 2 | $1 \times 10^8$ | 4/20 (20%) | | 9/20 (45%) | |
| Exp. 3 | $2 \times 10^8$ | | 9/24 (38%) | | 0/21 (100%) |

These results demonstrated that BombBC provided resistance to tobacco against *R. solanacearum*, and was 100% effective in seeded tobacco. These results, combined with the results from transgenic geraniums against two different pathogenic genera in Example 16, confirm the utility of using BombBC to control disease, not just in geraniums, but in transgenic plants generally.

Example 18

Use of BombBC Expressed in Transgenic Citrus and Tobacco Host Plants to Confer Resistance to *Candidatus* Liberibacter Asiaticus Citrus greening disease, or Huanglongbin, is caused by Ca. *Liberibacter asiaticus*. This uncultured bacterial pathogen is a USDA Select Agent. It is known to attack tobacco plants, which may be used as a proxy host to test genes for resistance against the bacterium in transgenic tobacco (Francischini et al., 2007). *Cuscuta* spp. (dodder) was used to transmit greening from a known positively infected source, a sweet orange plant, to each of 6 healthy plants of *Nicotiana tabacum* L. cv. *Xanthi*. Two of the tobacco plants were transgenic for BombBC (created using the methods of Examples 11 and 15) and the other four were controls. The tobacco plants were allowed to remain connected to dodder for 4 weeks, and the plants were assayed for greening by nested PCR as described (Zhou et al., 2007). Results were that three of the four control plants became symptomatic for greening and all three were PCR positive), and that neither of the two transgenic BombBC plants became symptomatic and neither were PCR positive. These plants were held for three weeks, and retested. The results were the same, and indicated that BombBC provides resistance against citrus greening disease.

Similar tests were performed using six healthy citrus Carrizo plants. Again, *Cuscuta* spp. (dodder) was used to transmit greening from a known positively infected source, a sweet orange plant, to each of 6 healthy plants of *Citrus sinensis*×

*Poncirus trifoliata*) cv. Carizzo. Two of the citrus plants were transgenic for BombBC (created using the methods of Example 12) and the other four were controls. The citrus plants were allowed to remain connected to dodder for 4 weeks, and the plants were assayed for greening by nested PCR as described (Zhou et al., 2007). Results were that none of the Carrizo plants became symptomatic for greening and only one control plant became PCR positive, and that neither of the two transgenic BombBC plants became PCR positive. These plants were held for three weeks, and retested. The results were the same, and again indicated that BombBC provides resistance against citrus greening disease

Example 19

Use of BombBC Expressed in Transgenic Citrus Host Plants to Confer Resistance to Citrus Canker Disease Six healthy *Citrus sinensis*×*Poncirus trifoliata*) cv. Carizzo plants were inoculated by dipping the entire top three inches of the 9-12 inch tall plants into a solution containing 200 ppm Silwet L-77 and *Xanthomonas citri* at $10^5$ cfu/ml. Symptoms on all plants appeared two weeks later, and were allowed to develop for four additional weeks. Two of the citrus plants were transgenic for BombBC (created using the methods of Example 12) and the other four were controls. Pathogenic symptoms caused by *X. citri* were greatly reduced in the two BombBC transgenic plants, both in terms of numbers of pustules (many fewer appeared in the BombBC plants) and in the size of the pustules (pustules remained tiny and were much less well developed in the BombBC plants).

These results confirmed and extended the concept that BombBC can be expressed in plants for the purpose of killing or disabling Gram-negative pathogenic bacteria to include host plants, most likely due to the combined effects of native phytoalexins produced by the host plant and expression of BombBC to compromise the LPS barrier of the pathogen.

Example 20

Use of Transgenic Rice Plants to Express Enzymatically Active BombBC

Transgenic rice plants expressing BombBC were created using *Agrobacterium tumefaciens* (Hiei et al., 1997) carrying the bombBC gene cloned into pIPG787. It is anticipated that these plants will be resistant to Gram negative bacterial pathogens, including *X. oryzae* and *X. oryzicola*.

Example 21

Method of Using Bomb Proteins Expressed in Transgenic Plants to Extend the Shelf-Life of Cut Flowers We anticipate that Bomb proteins, when produced in transgenic plants that are typically marketed as cut flowers, such as roses, carnations, chrysanthemums, gladiolas, etc., will enhance longevity of the cut transgenic flowers by suppressing bacterial growth in the vase water caused by opportunistic or soft-rotting bacteria such as *Erwinia carotovora* and *Erwinia chrysanthemi*. Transgenic plants that will later be marketed as cut flowers will be produced by methods described in the above examples.

Example 22

Method of Using Bomb Proteins as an Additive to Extend the Shelf Life of Cut Flowers and Animal Feed We anticipate that Bomb proteins, possibly in combination with lytic proteins, when added to the vase or shipping container water of nontransgenic plants that are typically marketed as cut flowers, such as roses, carnations, chrysanthemums, gladiolas, etc., will enhance longevity of the cut transgenic flowers by suppression of fungal and bacterial growth in the vase water. Typical microbial species that shorten the shelf life of cut flowers are *Erwinia carotovora* and *Erwinia chrysanthemi*. For example, we anticipate that adding a dried protein to water used to sustain cut flowers will result in a longer shelf-life for the cut flowers when compared to cut flowers sustained in water from the same source without the addition of the dried protein.

The Bomb proteins will most likely be produced in transgenic plants. Crude extracts of protein will be harvested, and either dried using a granular additive or suspended in an appropriate liquid and packaged. In another example, when the dried protein is added to animal feed, it will control microbial contamination, including those microbes that may cause food poisoning. A dry or liquid preparation of Bomb proteins could be added to animal feed during factory preparation or afterwards by the animal owner by mixing. Either way, the result will be a longer shelf life of the feed and reduced opportunity for growth of microbes that can result in food poisoning.

Example 23

Method of Using Bomb Proteins in Transgenic Plants to Control Gram-Negative Bacteria, Whether Disease Agents of Plants or not We anticipate that when transgenic plants producing Bomb proteins, possibly in combination with production of a lytic protein, are planted in field situations, they will exhibit resistance not only to Gram negative bacterial diseases of said plants through killing or inhibiting growth of these Gram negative bacteria, but also they will kill or inhibit growth of Gram negative bacteria such as *E. coli, Shigella* spp. and *Salmonella* spp. that may infect said plants, but without causing plant disease. Such transgenic plants may become part of a food security program aimed at reducing the possibility of spread of human diseases by food supply contamination. Resistance in all cases is anticipated to be achieved through the combined action of natural defense compounds produced by the transgenic plants and the Bomb proteins, together with any lytic enzymes produced by the transgenic plants.

It must be noted that as used in this specification and the appended claims, the singular forms “a,” “and,” and “the” include plural referents unless the contexts clearly dictates otherwise. Thus, for example, reference to “Bomb proteins” includes any one, two, or more of the Bomb proteins or fragments thereof, regardless of source; reference to “a transgenic plant” includes large numbers of transgenic plants and mixtures thereof, and reference to “the method” includes one or more methods or steps of the type described herein.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the exemplary methods and materials are described herein. All publications cited herein are incorporated herein by reference for the purpose of disclosing and describing specific aspects of the invention for which the publication is cited.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

LITERATURE CITED

Arce P et al. 1999. Enhanced resistance to bacterial infection by *Erwinia carotovora* subsp. *Atroseptica* in transgenic potato plants by expressing the attacin or the cecropin SB-37 genes. American Journal of Potato Research 76:169-177.

Bolton, E. T. and McCarthy, B. J. 1962. A general method for the isolation of RNA complementary to DNA. Proc. Natl. Acad. Sci. USA 48:1390.

Broekaert, W. F. et al. 1997. Antimicrobial peptides from plants. Critical Reviews in Plant Sciences 16:297-323.

Broothaerts, W. et al., 2005. Gene transfer to plants by diverse species of bacteria. Nature 433:629-633.

Callis, J., M. Fromm, and V. Walbot. 1987. Introns increase gene-expression in cultured maize cells. Genes & Development 1:1183-1200.

Calvo, M. V. and Fontecha, J. 2004. Purification and characterization of a pregastric esterase from a hygienized kid rennet paste. J. Dairy Sci. 87:1132-1142.

Ceccardi, T. L., G. A. Barthe, and K. S. Derrick. 1998. A novel protein associated with citrus blight has sequence similarities to expansin. Plant Molecular Biology 38:775-783.

Desnuelle, P. and Savary, P. 1963. Specificity of lipases. J. Lipid Research 4:309-384.

Doyle, M. P. 2000. Reducing foodborne disease: What are the priorities? Nutrition 16:647-649.

Duan Y P et al. 1999. Expression of a single, host-specific gene in citrus cells elicits division, enlargement and cell death. Molecular Plant-Microbe Interactions 12:556-560

During K et al. 1993. Transgenic potato plants resistant to the phytopathogenic bacterium *Erwinia carotovora*. Plant J 3:587-598

During, K., P. Porsch, A. Mahn, O. Brinkmann, and W. Gieffers. 1999. The non-enzymatic microbicidal activity of lysozymes. FEBS Letters 449:93-100.

Francischini et al., 2007. First Report on the Transmission of '*Candidatus* Liberibacter americanus' from Citrus to *Nicotiana tabacum* cv. *Xanthi*. Plant Disease 91:631.

Gabriel, D. W., Allen, C., Schell, M., Denny, T. P., Greenberg, J. T., Duan, Y. P., Flores-Cruz, Z., Huang, Q., Clifford, J. M., Presting, G., Gonzalez, E. T., Reddy, J. D., Elphinstone, J., Swanson, J., Yao, J., Mulholland, V., Liu, L., Farmerie, W., Patnaikuni, M., Balogh, B., Norman, D., Alvarez, A., Castillo, J. A., Jones, J., Saddler, G., Walunas, T., Zhukov, A., Mikhailova, N. 2006. Identification of open reading frames unique to a Select Agent: *Ralstoma solanacearum* race 3 biovar 2. Molec. Plant-Microbe Interact. 19:69-79.

Gruber, V., Berna, B. P., Arnaud, T., et al. 2001. Large-scale production of a therapeutic protein in transgenic tobacco plants: effect of subcellular targeting on quality of a recombinant dog gastric lipase. Molec. Breeding 7:329-340.

Gupta, R., Rathi, P., Gupta, N., Bradoo, S. 2003. Lipase assays for conventional and molecular screening: an overview. Biotechnol. Appl. Biochem. 37:63-71.

Hiei Y, Komari T, Kubo T., 1997. Transformation of rice mediated by *Agrobacterium tumefaciens*. Plant Mol. Biol. 35:205-18.

Horsch, R. B., Fry, J. E., Hoffmann, N. L., Eichholtz, D., Rogers, S. G. and Fraley, R. T. 1985. A simple and general method for transferring genes into plants. Science 227: 1229-1231.

Ibrahim, H. R., Thomas, U., and Pellegrini, A. 2001. A helix-loop-helix peptide at the upper lip of the active site cleft of lysozyme confers potent antimicrobial activity with membrane permeabilization action. J. Biol. Chem. 276:43767-43774.

Jaynes J M et al. 1987. Increasing bacterial disease resistance in plants utilizing antibacterial genes from insects. Bioassays 6:263-270

Jaeger, K. E. and Reetz, M. T. 1998. Microbial lipases form versatile tools for biotechnology. Trends Biotechnol. 16:396-403.

Jette, J. F. and Ziomek, E. 1994. Determination of lipase activity by a Rhodamine-Triglyceride-Agarose assay. Analytical Biochemistry 219:256-260.

Kapila, J., R. De Rycke, M. Van Montagu, and G. Angenon. 1997. An *Agrobacterium*-mediated transient gene expression system for intact leaves. Plant Science 122:101-108.

Kato, A., S, Nakamura, H. Ibrahim, T. Matsumi, C. Tsumiyama, and M. Kato. 1998. Production of genetically modified lysozymes having extreme heat stability and antimicrobial activity against Gram negative bacteria in yeast and in plant. Nahrung-Food 42:128-130.

Kingsley, M. T., D. W. Gabriel, G. C. Marlow, and P. D. Roberts. 1993. The opsX locus of *Xanthomonas campestris* affects host range and biosynthesis of lipopolysaccharide and extracellular polysaccharide. J. Bacteriol. 175: 5839-5850.

Ko K. 1999. Attacin and T4 lysozyme transgenic in Galaxy apple: Regulation of transgene expression and plant resistance to fire blight (*Erwinia amylovora*). PhD dissertation, Cornell University, Ithaca N.Y. 194 pp.

Ko K et al. 2000. Effect of untranslated leader sequence of AMV RNA 4 and signal peptide of pathogenesis-related protein 1b on attacin gene expression, and resistance to fire blight in transgenic apple. Biotechnology Letters 22:373-381 Li Q et al. 2001. Enhanced disease resistance conferred by expression of an antimicrobial magainin analog in transgenic tobacco. Planta 212:635-639.

Malnoy, M., Faize, M., Venisse, J. S, Geider, K., Chevreau, E., 2005. Expression of viral EPS-depolymerase reduces fire blight susceptibility in transgenic pear. Plant Cell Rep 23:632-638.

Mitra A and Zhang Z. 1994. Expression of a human lactoferrin cDNA in tobacco cells produces antibacterial protein(s). Plant Physiol 106:977-981.

Moore G. A., Jacono, C. C., Neidigh J. L., Lawrence S. D. and Cline K., 1992. *Agrobacterium*-mediated transformation of citrus stem segments and regeneration of transgenic plants. Plant Cell Rep 11:238-242.

Mun, J. H., Lee, S. Y., Yu, H. J., Jeong, Y. M., Shin, M. Y., Kim, H., Lee, I., and Kim, S. G. Petunia actin-depolymerizing factor is mainly accumulated in vascular tissue and its expression is enhanced by the first intron. Gene 292, 233-243. 2004.

Murashige, T. and Skoog, F. 1962. A revised medium for rapid growth and bioassays with tobacco tissue cultures. Physiol. Plant 15: 473-497.

Nakajima H et al. 1997. Fungal and bacterial disease resistance in transgenic plants expressing human lysozyme. Plant Cell Rep 16:674-679.

Norelli J L et al 1994. Transgenic Mailing 26 apple expressing the attacin E gene has increased resistance to *Erwinia amylovora*. Euphytica 77:123-128.

Norelli J L et al. 1998. Effect of cercropin-type transgenes on fire blight resistance of apple. Acta Hort 489:273-278.

Norelli J L et al. 1999. Genetic transformation for fire blight resistance in apple. Acta Hort 489:295-296.

Owens, L. D. and Heutte, T. M. (1997) A single amino acid substitution in the antimicrobial defense protein cecropin B is associated with diminished degradation by leaf intercellular fluid. Molecular Plant-Microbe Interactions. 10, 525-528.

Reddy, J D, Reddy, S L, Hopkins, D L, and Gabriel, D W. 2007. ToIC is required for pathogenicity of *Xylella fastidiosa* in grape plants. Molec. Plant-Microbe Interact. 20:403-410.

Reynoird J P et al. 1999. First evidence for differences in fire blight resistance among transgenic pear clones expressing attacin gene. Plant Science 149:23-31.

Riggs, C. D., K. Zeman, R. DeGuzman, A. Rzepczyk and A. A. Taylor. 2001. Antisense inhibition of a tomato meiotic proteinase suggests functional redundancy of proteinases during microsporogenesis Genome 44: 644-650.

Robichon, M. P., J. P. Renou and R. Jalouzot, 1995. Genetic transformation of *Pelargonium×hortorum*. Plant Cell Reports 15:63-67.

Rose, A. B. and Beliakoff, J. A. Intron-mediated enhancement of gene expression independent of unique intron sequences and splicing. Plant Physiol. 122, 535-542.2004.

Rose, A. B. 2002. Requirements for intron-mediated enhancement of gene expression in *Arabidopsis*. Rna-A Publication of the Rna Society 8:1444-1453.

Sambrook, J., Fritsch, E. F. and Maniatis, T., 1989. Molecular Cloning: A Laboratory Manual, Cold Spring Harbor Laboratory Press, NY Schmeller, T., Latz-Bruning, B., and Wink, M. 1997. Biochemical activities of berberine, palmatine and sanguinarine mediating chemical defence against microorganisms and herbivores. Phytochemistry 44:257-266

Segura, A., Moreno, M., Molina, A., Garcia-Olmedo, F., 1998. Novel defensin subfamily from spinach (*Spinacia oleracea*). FEBS Letters 435:159-162.

Shapiro, E., and Baneyx, F. 2002. Stress-based identification and classification of antibacterial agents: second generation *Escherichia coli* reporter strains and optimization of detection. Antimicrobial Agents Chemotherapy 46: 2490-2497.

Simpson, G. G. and Filipowicz, W. Splicing of precursors to mRNA in higher plants: mechanism, regulation an subnuclear organization of the spliceosomal machinery. Plant Mol. Biol. 32, 1-41.1996.

Singh, R., Gupta, N., Goswami, V. K. and R. Gupta. 2006. A simple activity staining protocol for lipases and esterases. Appl. Microbiol. Biotechnol. 70:679-682.

Taguchi S et al. 2000. Functional mapping against *Escherichia coli* for the broad-spectrum antimicrobial peptide, thanatin, based on an in vivo monitoring assay system. J Biochem 128:745-754.

Timmermans, M. Y. J., Teuchy, H., and Kupers, LPM. 1998. The cDNA sequence encoding boving pregastric esterase. Gene 147: 259-262.

Trudel J et al. 1995. Secreted hen lysozyme in transgenic tobacco: Recovery of bound enzyme and in vitro growth inhibition of plant pathogens. Plant Science 106:55-62.

Vunnam S et al. 1997. Synthesis and antibacterial action of cecropin and proline-arginine-rich peptides from pig intestine. J Peptide Res 49:59-66.

Wang Y et al. 1999. Porcine pulmonary surfactant preparations contain the antibacterial peptide prophenin and a C-terminal 18-residue fragment thereof. FEBS Lett 460: 257-262.

Wroblewski, T., Tomczak, A. and Michelmore, R. 2005. Optimization of *Agrobacterium* mediated transient assays of gene expression in lettuce, tomato and *Arabidopsis*. Plant Biotechnology J. 3:259-273.

Zhou, L. J., Gabriel, D. W., Duan, Y. P, Halbert, S., and Dixon, W. 2007. First Report of Dodder Transmission of Huanglongbing from Naturally Infected *Murraya paniculata* to Citrus. Plant Disease 91:227.

What is claimed is:

1. An isolated peptide, polypeptide or protein comprising:

a. the amino acid sequence of SEQ ID NO: 2;

b. an amino nucleic acid sequence with 95% amino acids sequence identity to of SEQ ID NO: 2 and which inhibits the growth of Gram negative bacteria in the presence of a phytoalexin;

c. an amino acid sequence encoded by a nucleic acid sequence which hybridizes to SEQ ID NO: 1 under stringent hybridization conditions with a wash of 0.1× SSC at 68° C. and which inhibits the growth of Gram negative bacteria in the presence of a phytoalexin; or d. an amino acid sequence encoded by a nucleic acid sequence having at least 95% or greater sequence identity to SEQ ID NO: 1 and which inhibits the growth of Gram negative bacteria in the presence of a phytoalexin.

2. A method of preventing, treating or reducing a Gram-negative bacterial infection or infestation of a plant cell, plant part, plant tissue or whole plant, said method comprising contacting the plant cell, plant part, plant tissue, or whole plant with the isolated peptide, polypeptide or protein of claim 1.

3. A composition comprising the isolated peptide, polypeptide or protein of claim 1.

4. A composition consisting essentially of the isolated peptide, polypeptide or protein of claim 1.

5. A composition consisting of the isolated peptide, polypeptide or protein of claim 1.

6. An isolated peptide, polypeptide or protein comprising an amino acid sequence having at least about 98% sequence identity to SEQ ID NO: 2 wherein the peptide, polypeptide or protein inhibits the growth of Gram negative bacteria in the presence of a phytoalexin.

7. An isolated peptide, polypeptide or protein comprising an amino acid sequence having at least about 99% sequence identity to SEQ ID NO: 2 wherein the peptide, polypeptide or protein inhibits the growth of Gram negative bacteria in the presence of a phytoalexin.

8. The isolated peptide, polypeptide or protein of claim 1, wherein the amino acid sequence has at least about 98% sequence identity to SEQ ID NO: 2.

9. The isolated peptide, polypeptide or protein of claim 1, wherein the amino acid sequence has at least about 99% sequence identity to SEQ ID NO: 2.

* * * * *

SEQUENCE LISTING

```
<160> NUMBER OF SEQ ID NOS: 5

<210> SEQ ID NO 1
<211> LENGTH: 510
<212> TYPE: DNA
<213> ORGANISM: X. pelargonii Phage P15

<400> SEQUENCE: 1

atgtccgacc agaccgatac cacccagacc acgccggccg agaaggcgcc gcccaaggaa      60

atcatccgcg gtcgtatgcc gatcgcagtg gtcgccctgg cccgcttcgg cagccagtcc     120

accaccacca ccaaggccgc agcggatgcc ctgggcacca ccgtcggcaa gatcgacgac     180

atccgcaaga accgcaactt cgcctacgtc accgccgact tcaagccgac cgaagcccag     240

aaggccgacg gcatcgagtg gctgaagcgt catccggtcg gtgcggatgc cctgatcgaa     300
```

-continued

```
gagctgcaga acctgccggt cgccaccgcc gaagagtcgg ccgcattcga gcaggtccgc    360

gcatcggctc gcggccagaa cgccaagacc gccgagggtg aagtcgctca ggccggcggt    420

ggcaatcgtc gcaagaagaa ggaaaagccg gccgaagccg gtgaagtgca gaacccgccg    480

gccgccgatg gcgactcgct cctgagctaa                                     510


<210> SEQ ID NO 2
<211> LENGTH: 169
<212> TYPE: PRT
<213> ORGANISM: X. pelargonii Phage P15

<400> SEQUENCE: 2

Met Ser Asp Gln Thr Asp Thr Thr Gln Thr Thr Pro Ala Glu Lys Ala
1               5                   10                  15

Pro Pro Lys Glu Ile Ile Arg Gly Arg Met Pro Ile Ala Val Val Ala
            20                  25                  30

Leu Ala Arg Phe Gly Ser Gln Ser Thr Thr Thr Thr Lys Ala Ala Ala
        35                  40                  45

Asp Ala Leu Gly Thr Thr Val Gly Lys Ile Asp Asp Ile Arg Lys Asn
    50                  55                  60

Arg Asn Phe Ala Tyr Val Thr Ala Asp Phe Lys Pro Thr Glu Ala Gln
65                  70                  75                  80

Lys Ala Asp Gly Ile Glu Trp Leu Lys Arg His Pro Val Gly Ala Asp
                85                  90                  95

Ala Leu Ile Glu Glu Leu Gln Asn Leu Pro Val Ala Thr Ala Glu Glu
            100                 105                 110

Ser Ala Ala Phe Glu Gln Val Arg Ala Ser Ala Arg Gly Gln Asn Ala
        115                 120                 125

Lys Thr Ala Glu Gly Glu Val Ala Gln Ala Gly Gly Gly Asn Arg Arg
    130                 135                 140

Lys Lys Lys Glu Lys Pro Ala Glu Ala Gly Glu Val Gln Asn Pro Pro
145                 150                 155                 160

Ala Ala Asp Gly Asp Ser Leu Leu Ser
                165


<210> SEQ ID NO 3
<211> LENGTH: 75
<212> TYPE: DNA
<213> ORGANISM: Unknown
<220> FEATURE:
<223> OTHER INFORMATION: P12 leader DNA sequence

<400> SEQUENCE: 3

atgggtgtag gcacaaaagt tctggtgatc acgaccatgg caatatgcct aattagctca     60

gctgcatatg cccat                                                      75


<210> SEQ ID NO 4
<211> LENGTH: 25
<212> TYPE: PRT
<213> ORGANISM: Unknown
<220> FEATURE:
<223> OTHER INFORMATION: P12 leader translation product

<400> SEQUENCE: 4

Met Gly Val Gly Thr Lys Val Leu Val Ile Thr Thr Met Ala Ile Cys
1               5                   10                  15

Leu Ile Ser Ser Ala Ala Tyr Ala His
            20                  25
```

-continued

```
<210> SEQ ID NO 5
<211> LENGTH: 193
<212> TYPE: PRT
<213> ORGANISM: Artificial Sequence
<220> FEATURE:
<223> OTHER INFORMATION: BombBC with P12 leader sequence, translation
      product

<400> SEQUENCE: 5

Met Gly Val Gly Thr Lys Val Leu Val Ile Thr Thr Met Ala Ile Cys
1               5                   10                  15

Leu Ile Ser Ser Ala Ala Tyr Ala Met Ser Asp Gln Thr Asp Thr Thr
            20                  25                  30

Gln Thr Thr Pro Ala Glu Lys Ala Pro Pro Lys Glu Ile Ile Arg Gly
        35                  40                  45

Arg Met Pro Ile Ala Val Val Ala Leu Ala Arg Phe Gly Ser Gln Ser
    50                  55                  60

Thr Thr Thr Thr Lys Ala Ala Ala Asp Ala Leu Gly Thr Thr Val Gly
65                  70                  75                  80

Lys Ile Asp Asp Ile Arg Lys Asn Arg Asn Phe Ala Tyr Val Thr Ala
                85                  90                  95

Asp Phe Lys Pro Thr Glu Ala Gln Lys Ala Asp Gly Ile Glu Trp Leu
            100                 105                 110

Lys Arg His Pro Val Gly Ala Asp Ala Leu Ile Glu Glu Leu Gln Asn
        115                 120                 125

Leu Pro Val Ala Thr Ala Glu Glu Ser Ala Ala Phe Glu Gln Val Arg
    130                 135                 140

Ala Ser Ala Arg Gly Gln Asn Ala Lys Thr Ala Glu Gly Glu Val Ala
145                 150                 155                 160

Gln Ala Gly Gly Gly Asn Arg Arg Lys Lys Lys Glu Lys Pro Ala Glu
                165                 170                 175

Ala Gly Glu Val Gln Asn Pro Pro Ala Ala Asp Gly Asp Ser Leu Leu
            180                 185                 190

Ser
```